US00RE45198E

(19) United States
(12) Reissued Patent
Phillips

(10) Patent Number: US RE45,198 E
(45) Date of Reissued Patent: Oct. 14, 2014

(54) OMEPRAZOLE SOLUTION AND METHOD FOR USING SAME

(75) Inventor: Jeffrey O. Phillips, Ashland, MO (US)

(73) Assignee: The Curators of The University Of Missouri, Columbia, MO (US)

(21) Appl. No.: 11/960,934

(22) Filed: Dec. 20, 2007

Related U.S. Patent Documents

Reissue of:
(64) Patent No.: 5,840,737
Issued: Nov. 24, 1998
Appl. No.: 08/680,376
Filed: Jul. 15, 1996

U.S. Applications:
(60) Provisional application No. 60/009,608, filed on Jan. 4, 1996.

(51) Int. Cl.
*A61K 31/4439* (2006.01)

(52) U.S. Cl.
USPC ..... 514/338

(58) Field of Classification Search
USPC ..... 514/338
See application file for complete search history.

(56) References Cited

U.S. PATENT DOCUMENTS

| | | | |
|---|---|---|---|
| 4,045,564 | A | 8/1977 | Berntsson et al. |
| 4,182,766 | A | 1/1980 | Krasso et al. |
| 4,252,790 | A | 2/1981 | Higuchi |
| 4,255,431 | A | 3/1981 | Junggren et al. |
| 4,337,257 | A | 6/1982 | Junggren et al. |
| 4,359,465 | A | 11/1982 | Ruwart |
| 4,414,216 | A | 11/1983 | Kawakita et al. |
| 4,472,409 | A | 9/1984 | Senn-Bilfinger |
| 4,508,905 | A | 4/1985 | Junggren et al. |
| 4,544,750 | A | 10/1985 | Brandstrom et al. |
| 4,613,497 | A | 9/1986 | Chavkin |
| 4,620,008 | A | 10/1986 | Brandstrom et al. |
| 4,628,098 | A | 12/1986 | Nohara et al. |
| 4,636,499 | A | 1/1987 | Brandstrom et al. |
| 4,689,333 | A | 8/1987 | Nohara et al. |
| 4,725,691 | A | 2/1988 | Brandstrom et al. |
| 4,738,974 | A | 4/1988 | Brandstrom |
| 4,786,505 | A | 11/1988 | Lovgren et al. |
| 4,853,230 | A | 8/1989 | Lovgren et al. |
| 4,965,351 | A | 10/1990 | Caruso et al. |
| 4,985,548 | A | 1/1991 | Caruso et al. |
| 4,990,535 | A | 2/1991 | Cho et al. |
| 5,008,278 | A | 4/1991 | Brandstrom et al. |
| 5,013,743 | A | 5/1991 | Iwahi et al. |
| 5,019,584 | A | 5/1991 | Brandstrom et al. |
| 5,025,024 | A | 6/1991 | Brandstrom et al. |
| 5,039,806 | A | 8/1991 | Brandstram et al. |
| 5,041,442 | A | 8/1991 | Romero et al. |
| 5,045,321 | A | 9/1991 | Makino et al. |
| 5,075,323 | A | 12/1991 | Fain et al. |
| 5,093,132 | A | 3/1992 | Makino et al. |
| 5,093,342 | A | 3/1992 | Tomoi et al. |
| 5,106,862 | A | 4/1992 | Briving et al. |
| 5,124,158 | A | 6/1992 | Ruwart et al. |
| 5,215,974 | A | 6/1993 | Alminger et al. |
| 5,219,870 | A | 6/1993 | Kim |
| 5,232,706 | A | 8/1993 | Palomo Coll |
| 5,244,670 | A | 9/1993 | Upson et al. |
| 5,254,682 | A | 10/1993 | Dhanoa et al. |
| 5,288,506 | A | 2/1994 | Spickett et al. |
| 5,294,439 | A | 3/1994 | Yamasaka et al. |
| 5,339,700 | A | 8/1994 | Wright et al. |
| 5,374,730 | A | 12/1994 | Slemon et al. |
| 5,385,739 | A | 1/1995 | Debregeas et al. |
| 5,386,032 | A | 1/1995 | Brandstrom |
| 5,391,752 | A | 2/1995 | Hoerner et al. |
| 5,395,323 | A | 3/1995 | Berglund |
| 5,399,700 | A | 3/1995 | Min et al. |
| 5,417,980 | A | 5/1995 | Goldman et al. |
| 5,430,042 | A | 7/1995 | Lindberg et al. |
| 5,443,826 | A | 8/1995 | Borody |
| 5,447,918 | A | 9/1995 | McCullough |

(Continued)

FOREIGN PATENT DOCUMENTS

| | | |
|---|---|---|
| CA | 1234118 | 3/1988 |
| CA | 2378018 A1 | 1/2001 |

(Continued)

OTHER PUBLICATIONS

Zhao et al., "Chronic Helicobacter, etc.," Regulatory Peptides 115 (2003) 161-170.*

(Continued)

*Primary Examiner* — Patricia L Morris
(74) *Attorney, Agent, or Firm* — Mayer Brown LLP

(57) ABSTRACT

A pharmaceutical composition includes an aqueous solution/suspension of omeprazole or other substituted benzimidazoles and derivatives thereof in a pharmaceutically acceptable carrier comprising a bicarbonate salt of a Group IA metal. A method for treating and/or preventing gastrointestinal conditions by administering to a patient a pharmaceutical composition including an aqueous solution/suspension of omeprazole or other substituted benzimidazoles and derivatives thereof in a pharmaceutically acceptable carrier including a bicarbonate salt of a Group IA metal wherein the administering step consists of a single dosage form without requiring further administering of the bicarbonate salt of the Group IA metal. A pharmaceutical composition for making a solution/suspension of omeprazole or other substituted benzimidazoles and derivatives thereof includes omeprazole or other substituted benzimidazoles and derivatives thereof and a bicarbonate salt of a Group IA metal in a form for convenient storage whereby when the composition is dissolved in aqueous solution, the resulting solution is suitable for enteral administration.

24 Claims, 1 Drawing Sheet

(56) References Cited

U.S. PATENT DOCUMENTS

| | | | |
|---|---|---|---|
| 5,633,244 | A | 5/1997 | Eek et al. |
| 5,639,478 | A | 6/1997 | Makino et al. |
| 5,690,960 | A | 11/1997 | Bengtsson et al. |
| 5,693,818 | A | 12/1997 | Von Unge |
| 5,703,097 | A | 12/1997 | Kim et al. |
| 5,714,504 | A | 2/1998 | Lindberg et al. |
| 5,714,505 | A | 2/1998 | Hasselkus |
| 5,731,002 | A | 3/1998 | Olovson et al. |
| 5,753,265 | A | 5/1998 | Bergstrand et al. |
| 5,762,962 | A | 6/1998 | Georgiades et al. |
| 5,766,622 | A | 6/1998 | Nelson |
| 5,776,765 | A | 7/1998 | Graham et al. |
| 5,798,120 | A | 8/1998 | Tomohisa et al. |
| 5,814,338 | A | 9/1998 | Veronesi |
| 5,817,338 | A | 10/1998 | Bergstrand et al. |
| 5,840,737 | A | 11/1998 | Phillips |
| 5,876,759 | A | 3/1999 | Gowan, Jr. |
| 5,877,192 | A | 3/1999 | Lindberg et al. |
| 5,879,708 | A | 3/1999 | Makino et al. |
| 5,883,102 | A | 3/1999 | Hamley et al. |
| 5,885,594 | A | 3/1999 | Nilson et al. |
| 5,900,424 | A | 5/1999 | Kallstrom et al. |
| 5,929,244 | A | 7/1999 | Von Unge |
| 5,939,091 | A | 8/1999 | Eoga et al. |
| 5,948,789 | A | 9/1999 | Larsson et al. |
| 5,955,107 | A | 9/1999 | Augello et al. |
| 5,958,955 | A | 9/1999 | Gustavsson et al. |
| 5,962,022 | A | 10/1999 | Bolt et al. |
| 5,965,162 | A | 10/1999 | Fuisz et al. |
| 5,972,389 | A | 10/1999 | Shell et al. |
| 5,979,515 | A | 11/1999 | Olsson |
| 6,013,281 | A | 1/2000 | Lundberg et al. |
| 6,017,560 | A | 1/2000 | Makino et al. |
| 6,068,859 | A | 5/2000 | Curatolo et al. |
| 6,090,827 | A | 7/2000 | Erickson et al. |
| 6,123,962 | A | 9/2000 | Makino et al. |
| 6,124,464 | A | 9/2000 | Hogberg et al. |
| 6,132,770 | A | 10/2000 | Lundberg |
| 6,132,771 | A | 10/2000 | Depui et al. |
| 6,136,344 | A | 10/2000 | Depui et al. |
| 6,143,771 | A | 11/2000 | Lindberg et al. |
| 6,147,103 | A | 11/2000 | Anousis et al. |
| 6,150,380 | A | 11/2000 | Lovqvist et al. |
| 6,162,816 | A | 12/2000 | Bohlin et al. |
| 6,166,213 | A | 12/2000 | Anousis et al. |
| 6,183,776 | B1 | 2/2001 | Depui et al. |
| 6,248,363 | B1 | 6/2001 | Patel et al. |
| 6,262,085 | B1 | 7/2001 | Whittle et al. |
| 6,262,086 | B1 | 7/2001 | Whittle et al. |
| 6,268,385 | B1 | 7/2001 | Whittle et al. |
| 6,274,173 | B1 | 8/2001 | Sachs et al. |
| 6,280,773 | B1 | 8/2001 | Cho et al. |
| 6,284,271 | B1 | 9/2001 | Lundberg et al. |
| 6,328,993 | B1 | 12/2001 | Linder et al. |
| 6,489,346 | B1 | 12/2002 | Phillips et al. |
| 6,569,453 | B2 | 5/2003 | Linder et al. |
| 6,608,091 | B2 | 8/2003 | Whittall et al. |
| 6,608,092 | B1 | 8/2003 | Fujishima et al. |
| 6,608,210 | B2 | 8/2003 | Naka et al. |
| 6,623,759 | B2 | 9/2003 | Heese et al. |
| 6,645,988 | B2 | 11/2003 | Phillips |
| 6,649,609 | B2 | 11/2003 | Teuber et al. |
| 6,664,276 | B2 | 12/2003 | Fujishima et al. |
| 6,669,885 | B2 | 12/2003 | Kasai et al. |
| 6,677,455 | B2 | 1/2004 | Kronstrom et al. |
| 6,699,885 | B2 | 3/2004 | Phillips |
| 6,749,867 | B2 | 6/2004 | Robinson et al. |
| 6,780,882 | B2 | 8/2004 | Phillips |
| 2001/0053387 | A1 | 12/2001 | Hamied et al. |
| 2002/0025342 | A1 | 2/2002 | Linder et al. |
| 2002/0192299 | A1 | 12/2002 | Taneja et al. |
| 2003/0118669 | A1 | 6/2003 | Phillips |
| 2003/0144306 | A1 | 7/2003 | Phillips |
| 2003/0181457 | A1 | 9/2003 | Orme et al. |
| 2003/0199580 | A1 | 10/2003 | Kishi et al. |
| 2003/0211147 | A1 | 11/2003 | Cullen et al. |
| 2003/0215527 | A1 | 11/2003 | Phillips |
| 2003/0225136 | A1 | 12/2003 | Whittle et al. |
| 2004/0010151 | A1 | 1/2004 | Finkelstein et al. |
| 2004/0048896 | A1 | 3/2004 | Phillips |
| 2004/0058018 | A1 | 3/2004 | Phillips |
| 2004/0171646 | A1 | 9/2004 | Phillips |
| 2005/0004171 | A1 | 1/2005 | Phillips |
| 2005/0037070 | A1 | 2/2005 | Hall et al. |
| 2005/0042304 | A1 | 2/2005 | Phillips |
| 2005/0054682 | A1 | 3/2005 | Phillips |

FOREIGN PATENT DOCUMENTS

| | | | |
|---|---|---|---|
| CA | 2432184 | A1 | 7/2002 |
| DE | 19752843 | A1 | 7/1999 |
| EP | 0005129 | A1 | 10/1979 |
| EP | 005129 | B1 | 4/1981 |
| EP | 0040639 | A1 | 12/1981 |
| EP | 0040639 | B1 | 5/1984 |
| EP | 0237200 | A2 | 9/1987 |
| EP | 0244380 | A2 | 11/1987 |
| EP | 0247983 | A2 | 12/1987 |
| EP | 0248634 | A2 | 12/1987 |
| EP | 0315964 | A1 | 11/1988 |
| EP | 0308515 | A1 | 3/1989 |
| EP | 0394471 | A1 | 10/1990 |
| EP | 0452697 | A1 | 10/1991 |
| EP | 0465254 | A1 | 1/1992 |
| EP | 0480691 | A2 | 4/1992 |
| EP | 0237200 | B1 | 7/1992 |
| EP | 0496437 | A2 | 7/1992 |
| EP | 0496437 | A3 | 7/1992 |
| EP | 0502556 | A1 | 9/1992 |
| EP | 0244380 | B1 | 1/1993 |
| EP | 0247983 | B1 | 1/1993 |
| EP | 0315964 | B1 | 1/1993 |
| EP | 0248634 | B1 | 7/1993 |
| EP | 0414847 | B1 | 9/1993 |
| EP | 0338861 | B1 | 10/1993 |
| EP | 0565210 | A2 | 10/1993 |
| EP | 0567201 | A2 | 10/1993 |
| EP | 0567201 | A3 | 10/1993 |
| EP | 0567643 | A1 | 11/1993 |
| EP | 0308515 | B1 | 1/1994 |
| EP | 0584588 | A1 | 3/1994 |
| EP | 0436620 | B1 | 8/1994 |
| EP | 0654471 | A1 | 5/1995 |
| EP | 0565210 | A3 | 6/1995 |
| EP | 0670160 | A1 | 9/1995 |
| EP | 0452697 | B1 | 12/1995 |
| EP | 0502556 | B1 | 6/1996 |
| EP | 0496437 | B1 | 7/1996 |
| EP | 0652751 | B1 | 10/1996 |
| EP | 0587659 | B1 | 5/1997 |
| EP | 0654471 | B1 | 7/1998 |
| EP | 0567201 | B1 | 9/1999 |
| EP | 0565210 | B1 | 11/1999 |
| EP | 1004305 | A1 | 5/2000 |
| EP | 0636364 | B1 | 9/2000 |
| EP | 1043977 | B1 | 10/2000 |
| EP | 0696921 | B1 | 2/2001 |
| EP | 1375497 | B1 | 9/2006 |
| ES | 2024993 | A1 | 3/1992 |
| GB | 2189698 | A | 11/1987 |
| JP | 45-39541 | B | 12/1970 |
| JP | 45-39543 | B | 12/1970 |
| JP | 46-9580 | B | 3/1971 |
| JP | 46-9581 | B | 3/1971 |
| JP | 48-103567 | A | 12/1973 |
| JP | 49-5967 | A | 1/1974 |
| JP | 49-13172 | A | 2/1974 |
| JP | 49-20173 | A | 2/1974 |
| JP | 49-20174 | A | 2/1974 |
| JP | 49-41198 | B | 4/1974 |
| JP | 49-93537 | A | 9/1974 |
| JP | 49-95997 | A | 9/1974 |
| JP | 50-52065 | A | 5/1975 |
| JP | 50-112373 | A | 9/1975 |

(56) References Cited

FOREIGN PATENT DOCUMENTS

| | | | |
|---|---|---|---|
| JP | 50-142565 | A | 11/1975 |
| JP | 51-16669 | A | 2/1976 |
| JP | 51-17268 | | 2/1976 |
| JP | 51-131875 | A | 11/1976 |
| JP | 52-5769 | | 1/1977 |
| JP | 52-14776 | A | 2/1977 |
| JP | 52-97978 | A | 8/1977 |
| JP | 52-102416 | A | 8/1977 |
| JP | 53-59675 | A | 5/1978 |
| JP | 55-19211 | A | 2/1980 |
| JP | 56-61311 | A | 5/1981 |
| JP | 59-95997 | A | 6/1984 |
| JP | 61-221117 | A | 10/1986 |
| JP | 62-145083 | A | 6/1987 |
| JP | 62-258316 | A | 11/1987 |
| JP | 62-258320 | A | 11/1987 |
| JP | 62-277322 | A | 12/1987 |
| JP | 62-283964 | A | 12/1987 |
| JP | 02022225 | A | 1/1990 |
| JP | 03034967 | A | 2/1991 |
| JP | 03048680 | A | 3/1991 |
| JP | 03052887 | A | 3/1991 |
| JP | 03163018 | A | 7/1991 |
| JP | 05117268 | A | 5/1993 |
| JP | 05194224 | A | 8/1993 |
| JP | 05194225 | A | 8/1993 |
| JP | 05255088 | A | 10/1993 |
| JP | 05294831 | A | 11/1993 |
| JP | 06092853 | A | 4/1994 |
| JP | 06100449 | A | 4/1994 |
| JP | 09087110 | A | 3/1997 |
| JP | 10017470 | A | 1/1998 |
| JP | 10017471 | A | 1/1998 |
| JP | 2000212180 | A2 | 8/2000 |
| JP | 2000355540 | A2 | 12/2000 |
| JP | 07033659 | A | 2/2005 |
| KR | 1996-0003605 | B | 3/1996 |
| KR | 1996-0011238 | B | 8/1996 |
| KR | 1996-0011390 | B | 8/1996 |
| RO | 88351 | | 4/1986 |
| WO | WO-89/00566 | A1 | 1/1989 |
| WO | WO-90/03184 | A1 | 4/1990 |
| WO | WO-90/09175 | A1 | 8/1990 |
| WO | WO-92/04898 | A1 | 4/1992 |
| WO | WO-92/08716 | A1 | 5/1992 |
| WO | WO-92/21331 | A1 | 12/1992 |
| WO | WO-93/05770 | A1 | 4/1993 |
| WO | WO-93/13138 | A1 | 7/1993 |
| WO | WO-95/01783 | A1 | 11/1993 |
| WO | WO-95/07913 | A1 | 11/1993 |
| WO | WO-94/00112 | A1 | 1/1994 |
| WO | WO-94/02140 | A1 | 2/1994 |
| WO | WO-94/02141 | A1 | 2/1994 |
| WO | WO-95/15962 | A1 | 6/1995 |
| WO | WO-95/23594 | A1 | 9/1995 |
| WO | WO-95/32957 | A1 | 12/1995 |
| WO | WO-95/32958 | A1 | 12/1995 |
| WO | WO-95/32959 | A1 | 12/1995 |
| WO | WO-96/01612 | A1 | 1/1996 |
| WO | WO-96/01622 | A1 | 1/1996 |
| WO | WO-96/01623 | A1 | 1/1996 |
| WO | WO-96/01624 | A1 | 1/1996 |
| WO | WO-96/01625 | A1 | 1/1996 |
| WO | WO-96/02236 | A1 | 2/1996 |
| WO | WO-96/16959 | A1 | 6/1996 |
| WO | WO-96/24375 | A1 | 8/1996 |
| WO | WO-96/24388 | A1 | 8/1996 |
| WO | WO-96/38175 | A1 | 12/1996 |
| WO | WO-97/02020 | A1 | 1/1997 |
| WO | WO-97/02021 | A1 | 1/1997 |
| WO | WO-97/09964 | A1 | 3/1997 |
| WO | WO-97/25030 | A1 | 7/1997 |
| WO | WO-97/25064 | A1 | 7/1997 |
| WO | WO-97/25065 | A1 | 7/1997 |
| WO | WO-97/25066 | A1 | 7/1997 |
| WO | WO-97/41114 | A1 | 11/1997 |
| WO | WO-97/48380 | A1 | 12/1997 |
| WO | WO-98/00114 | A2 | 1/1998 |
| WO | WO-98/02368 | A1 | 1/1998 |
| WO | WO-98/16228 | A1 | 4/1998 |
| WO | WO-98/28294 | A1 | 7/1998 |
| WO | WO-98/40054 | A1 | 9/1998 |
| WO | WO-98/50019 | A1 | 11/1998 |
| WO | WO-98/53803 | A1 | 12/1998 |
| WO | WO-98/54171 | A1 | 12/1998 |
| WO | WO-99/00380 | A1 | 1/1999 |
| WO | WO-99/08500 | A2 | 2/1999 |
| WO | WO-99/25323 | A1 | 5/1999 |
| WO | WO-99/25711 | A1 | 5/1999 |
| WO | WO-99/27917 | A1 | 6/1999 |
| WO | WO-99/29299 | A1 | 6/1999 |
| WO | WO-99/29320 | A1 | 6/1999 |
| WO | WO-99/32091 | A1 | 7/1999 |
| WO | WO-99/32093 | A1 | 7/1999 |
| WO | WO-99/36060 | A1 | 7/1999 |
| WO | WO-99/45004 | A1 | 9/1999 |
| WO | WO-99/53918 | A1 | 10/1999 |
| WO | WO-99/55705 | A1 | 11/1999 |
| WO | WO-99/55706 | A1 | 11/1999 |
| WO | WO-0001372 | A2 | 1/2000 |
| WO | WO-0001372 | A3 | 1/2000 |
| WO | WO-0009092 | A1 | 2/2000 |
| WO | WO-0010999 | A2 | 3/2000 |
| WO | WO-0010999 | A3 | 3/2000 |
| WO | WO-0015195 | A1 | 3/2000 |
| WO | WO-0026185 | A2 | 5/2000 |
| WO | WO-0026185 | A3 | 5/2000 |
| WO | WO-0027366 | A1 | 5/2000 |
| WO | WO-0028975 | A2 | 5/2000 |
| WO | WO-0028975 | A3 | 5/2000 |
| WO | WO-0030612 | A1 | 6/2000 |
| WO | WO-0035448 | A1 | 6/2000 |
| WO | WO-0044744 | A1 | 8/2000 |
| WO | WO-0045817 | A1 | 8/2000 |
| WO | WO-0050038 | A1 | 8/2000 |
| WO | WO-0069438 | A1 | 11/2000 |
| WO | WO-0078293 | A1 | 12/2000 |
| WO | WO-0113919 | A1 | 3/2001 |
| WO | WO-0124780 | A2 | 4/2001 |
| WO | WO-0134573 | A1 | 5/2001 |
| WO | WO-0151050 | A1 | 7/2001 |
| WO | WO-0103707 | A1 | 1/2002 |
| WO | WO-03009846 | A1 | 2/2003 |
| WO | WO-03017980 | A1 | 3/2003 |
| WO | WO-03061584 | A2 | 7/2003 |
| WO | WO-03063927 | A2 | 8/2003 |

OTHER PUBLICATIONS

Coruzzi et al., "Gastric Antisecretory, etc.," Gen. Pharmac. 26 (5), pp. 1027-1032, 1995.*

Richardson et al., "Proton Pump, etc.," Drugs Sep. 1998: 56(3), 307-335.*

Ansel, et al., Pharmaceutical Dosage Forms and Drug Delivery Systems, p. 77, Williams & Wilkins, 6th ed. (1995).

Bader, et al., "An Open Trial of Omeprazole in Short-Term Treatment of Duodenal Ulcer", Scand. J. Gastroenterology, vol. 21, Suppl. 118, pp. 177-178 (1986).

Baron, et al., "Discussion", Scand. J. Gastroenterology, vol. 21, Suppl. 118, p. 117. (1986).

Baron, et al., "Discussion", Scand. J. Gastroenterology, vol. 21, Suppl. 118, p. 122 (1986).

Bendtsen, et al., "Intraduodenal pH During Omeprazole Treatment in Duodenal Ulcer Patients", Scand. J. Gastroenterology, vol. 21, Suppl. 118, pp. 156-157 (1986).

Berglindh, Thomas, "How to Study Properties of a Terminal Step Acid-Secretory Inhibitor In Vitro", Scand. J. Gastroenterology, vol. 21, Suppl. 118, pp. 47-48 (1986).

Berglindh, et al., "Discussion", Scand. J. Gastroenterology, vol. 21, Suppl. 118, p. 96-98 (1986).

Blom, Hakan, "Effects of Omeprazole on Normal and Regenerating Gastric Mucosa in the Rat. A Light and Electron Microscopic Study", Scand. J. Gastroenterology, vol. 21, Suppl. 118, pp. 70-71 (1986).

(56) References Cited

OTHER PUBLICATIONS

Blum, et al., "Discussion", Scand. J. Gastroenterology, vol. 21, Suppl. 118, p. 134-135(1986).
Brandstrom, et al., "Structure-Activity Relationship of Substituted Benzimidazoles", Scand. J. Gastroenterology, vol. 21, Suppl. 118, pp. 54-56 (1986).
Byrod, Eva, "Direction for Use of Omeprazole", pp. 1-3.
Carlsson, et al., "Pharmacology and Toxicology of Omeprazole with Special Reference to the Effects on Gastric Mucosa", Scand. J. Gastroenterology, vol. 21, Suppl. 118, pp. 31-38 (1986).
Colin-Jones, et al., "Discussion", Scand. J. Gastroenterology, vol. 21, Suppl. 118, p. 128 (1986).
Colin-Jones, et al., "Discussion", Scand. J. Gastroenterology, vol. 21, Suppl. 118, pp. 187-194 (1986).
Crean, et al., "Discussion", Scand. J. Gastroenterology, vol. 21, Suppl. 118, p. 46 (1986).
Damman, et al., "Intragastric Acidity Under a 28-Day Omeprazole Treatment", Scand. J. Gastroenterology, vol. 21, Suppl. 118, pp. 154-155 (1986).
Darle, et al., "Rate of Healing of Benign Gastric Ulcer During Treatment with Omeprazole", Scand. J. Gastroenterology, vol. 21, Suppl. 118, p. 180 (1986).
Delchier, et al., "Long-Term Treatment with Omeprazole in Seven Patients with Zollinger-Ellison Syndrome Resistant to $H_2$-Antagonists", Scand. J. Gastroenterology, vol. 21, Suppl. 118, pp. 184-186 (1986).
Dent, et al., "Effects of Omeprazole on Peptic Oesophagitis and Oesophageal Motility and pH", Scand. J. Gastroenterology, vol. 21, Suppl. 118, p. 181 (1986).
Dive, et al., "Rate of Duodenal Ulcer Healing During Treatment with Omeprazole. A Double-Blind Comparison of a Daily Dose of 30 mg Versus 60 mg", Scand. J. Gastroenterology, vol. 21, Suppl. 118, pp. 175-176 (1986).
Earnest, David, "Controlling Gastric pH: The Impact of Newer Agents on the Critically Ill Patient", DICP Ann. Pharmacother., vol. 24 (Suppl.), pp. S31-S34 (1990).
Festen, et al., "The Effect of Oral Omeprazole on Gastric Acid and Pepsin Secretion", Scand. J. Gastroenterology, vol. 21, Suppl. 118, pp. 158-159 (1986).
Festen, et al., "Effect of Oral Omeprazole on Fasting and Meal Stimulated Serum Gastrin and Serum Pepsinogen I Levels in Healthy Volunteers", Scand. J. Gastroenterology, vol. 21, Suppl. 118, pp. 160-161 (1986).
Fimmel, et al., "The Effects of Omeprazole on Acid and Pepsin Secretion in the Isolated, In Vitro Perfused Whole Mouse Stomach", Scand. J. Gastroenterology, vol. 21, Suppl. 118, pp. 68-69 (1986).
Flemstrom, et al., "Effects of Omeprazole on Gastric and Duodenal Bicarbonate Secretion", Scand. J. Gastroenterology, vol. 21, Suppl. 118, pp. 65-67 (1986).
Forssell, et al., "Structure and Function of the Dog Gastric Mucosa During and After a 1-Year Treatment with Omeprazole. I. Macro- and Microscopic Findings", Scand. J. Gastroenterology, vol. 21, Suppl. 118, pp. 79-81 (1986).
Hakanson, et al., "Gastrin and the Trophic Control of Gastric Mucosa", Scand. J. Gastroenterology, vol. 21, Suppl. 118, pp. 18-30 (1986).
Hansson, et al., "Toxicology Studies with Omeprazole", Scand. J. Gastroenterology, vol. 21, Suppl. 118, pp. 89-91 (1986).
Howden, et al., "An Investigation into the Effects of Omeprazole on Renal Tubular Function and Endocrine Function in Man", Scand. J. Gastroenterology, vol. 21, Suppl. 118, pp. 169-170 (1986).
Huttemann, W., "Short-Term Treatment of Gastric Ulcer with Once Daily Omeprazole", Scand. J. Gastroenterology, vol. 21, Suppl. 118, p. 179 (1986).
Kittang, et al., "Effect of Omeprazole on the Secretion of Intrinsic Factor, Gastric Juice and Pepsin in Man", Scand. J. Gastroenterology, vol. 21, Suppl. 118, pp. 162-163 (1986).
Lamers, Cornelis, "Present Experiences with Omeprazole in the Zollinger-Ellison Syndrome", Scand. J. Gastroenterology, vol. 21, Suppl. 118, pp. 123-127 (1986).
Larsen, et al., "Effects of Omeprazole and Cimetidine on Mucosal Acid Secretion, Blood Flow and Oxygen Consumption in the Dog Ex Vivo Gastric Chamber", Scand. J. Gastroenterology, vol. 21, Suppl. 118, pp. 61-64 (1986).
Larsson, et al., "Animal Pharmacodynamics of Omeprazole. A Survey of its Pharmacological Properties in vivo", Scand. J. Gastroenterology, vol. 20, Suppl. 108, pp. 23-35 (1985).
Larsson, et al., "Inhibition of Rat Gastric $H^+$-$K^+$-ATPase In Vivo. Relation to Reduction of Acid Secretion", Scand. J. Gastroenterology, vol. 21, Suppl. 118, pp. 57-58 (1986).
Lind, et al., "Long-Term Acid Inhibitory Effect of Different Daily Doses of Omeprazole 24 Hours After Dosing", Scand. J. Gastroenterology, vol. 21, Suppl. 118, pp. 137-138 (1986).
Mardh, Sven, "Omeprazole Inhibits the Formation of Acid in the Parietal Cell by a Direct Inhibition of the $H^+$-$K^+$-ATPase, the Acid Pump of the Stomach", Scand. J. Gastroenterology, vol. 21, Suppl. 118, pp. 49-51 (1986).
Mattsson, et al., "Effect of Omeprazole on Gastric Mucosal Blood Flow in the Rat", Scand. J. Gastroenterology, vol. 21, Suppl. 118, pp. 72-74 (1986).
Mattsson, Hillevi, "Protective Effects of Omeprazole in the Gastric Mucosa", Scand. J. Gastroenterology, vol. 21, Suppl. 118, pp. 86-88 (1986).
McArthur, et al., "Omeprazole: An Effective Drug for Zollinger-Ellison Syndrome", Scand. J. Gastroenterology, vol. 21, Suppl. 118, pp. 182-183 (1986).
Muller, et al., "Acid Secretion During and After Omeprazole Treatment in Healthy Volunteers", Scand. J. Gastroenterology, vol. 21, Suppl. 118, pp. 141-142 (1986).
Naesdal, et al., "Diurnal Intragastric Acidity During Omeprazole Treatment in Patients with Peptic Ulcer Disease", Scand. J. Gastroenterology, vol. 21, Suppl. 118, pp. 150-151 (1986).
Nielsen, et al., "Immediate Effect of Omeprazole and Cimetidine on Apparent Liver Blood Flow in Man", Scand. J. Gastroenterology, vol. 21, Suppl. 118, pp. 166-168 (1986).
Okabe, et al., "Effects of Omeprazole on Gastric Secretion and Experimental Ulcers in Rats", Scand. J. Gastroenterology, vol. 21, Suppl. 118, pp. 75-76 (1986).
Olbe, et al., "Effect of Omeprazole on Gastric Acid Secretion in Man", Scand. J. Gastroenterology, vol. 21, Suppl. 118, pp. 105-107 (1986).
Peckman, "Alternative Method for Administering Proton-Pump Inhibitors Through Nasogastric Tubes", American Journal of Health-System Pharmacists, vol. 56, p. 1020 (May 15, 1999).
Poulsen, et al., "Omeprazole Accelerates Healing of Cysteamine Induced Duodenal Ulcers in Rat", Scand. J. Gastroenterology, vol. 21, Suppl. 118, pp. 77-78 (1986).
Pounder, et al., "Twenty-Four Hour Intragastric Acidity during Treatment with Oral Omeprazole", Scand. J. Gastroenterology, vol. 21, Suppl. 118, pp. 108-116 (1986).
Prilosec Production Information, Rev. Jul. 2005, submitted with NDA 19-810.
Regardh, C.S., "Pharmacokinetics and Metabolism of Omeprazole in Man", Scand. J. Gastroenterology, vol. 21, Suppl. 118, pp. 99-104 (1986).
Rohner, et al., "Oral Omeprazole, 20 mg Versus 30 mg Once Daily: Effect on Healing Rates in 115 Duodenal Ulcer Patients", Scand. J. Gastroenterology, vol. 21, Suppl. 118, pp. 173-174 (1986).
Ryberg, et al., "Gastric Acid Secretion and Plasma Gastrin Levels in Dogs Treated with High Oral Doses of Ranitidine and Omeprazole", Scand. J. Gastroenterology, vol. 21, Suppl. 118, pp. 94-95 (1986).
Sachs, George, "The Parietal Cell as a Therapeutic Target", Scand. J. Gastroenterology, vol. 21, Suppl. 118, pp. 1-10 (1986).
Sachs, et al., "Discussion", Scand. J. Gastroenterology, vol. 21, Suppl. 118, p. 17 (1986).
Sewing, et al., "Effect of Substituted Benzimidazoles on $H^{+-K+}$-ATPase of Isolated Guinea-pig Parietal Cells", Scand. J. Gastroenterology, vol. 21, Suppl. 118, pp. 52-53 (1986).
Sharma, et al., "Acid Secretory Capacity After Treatment with Omeprazole", Scand. J. Gastroenterology, vol. 21, Suppl. 118, pp. 143-144 (1986).

(56) References Cited

OTHER PUBLICATIONS

Shearman, et al., "The Inhibition of Nocturnal Gastric Acid Secretion by Omeprazole in Patients with Duodenal Ulcer", Scand. J. Gastroenterology, vol. 21, Suppl. 118, pp. 145-146 (1986).
Shearman, et al., "Effect of Omeprazole on Gastric Emptying in Patients with a History of Duodenal Ulceration", Scand. J. Gastroenterology, vol. 21, Suppl. 118, pp. 164-165 (1986).
Skanberg, et al., "Pharmacokinetics and Metabolism of Omeprazole in Animals", Scand. J. Gastroenterology, vol. 21, Suppl. 118, pp. 92-93. (1986).
Smallwood, et al., "Double-Blind Comparison of Omeprazole, 10 mg Versus 30 mg, for Healing Duodenal Ulcers", Scand. J. Gastroenterology, vol. 21, Suppl. 118, pp. 171-172 (1986).
Solvell, Lennart, "Safety Aspects of Omeprazole", Scand. J. Gastroenterology, vol. 21, Suppl. 118, pp. 129-133 (1986).
Sundell, et al., "Structure and Function of the Dog Gastric Mucosa During and After a 1-Year Treatment with Omeprazole. II. Effects on Gastric Acid Secretion and Blood Levels of Gastric Hormones", Scand. J. Gastroenterology, vol. 21, Suppl. 118, pp. 82-85 (1986).
Sundler, et al., "Inhibition of Gastric Acid Secretion by Omeprazole and Ranitidine. Effects on Plasma Gastrin and Gastric Histamine, Histidine Decarboxylase Activity and ECL Cell Density in Normal and Antrectomized Rats", Scand. J. Gastroenterology, vol. 21, Suppl. 118, pp. 39-45 (1986).
Uusitalo, et al., "Effect of Omeprazole on Ulcer Healing and Pentagastrin Stimulated Acid Secretion During and After Treatment in Patients with Duodenal Ulcer", Scand. J. Gastroenterology, vol. 21, Suppl. 118, pp. 139-140 (1986).
Walan, Anders, "Treatment of Duodenal Ulcer Disease. Clinical Results with Omeprazole", Scand. J. Gastroenterology, vol. 21, Suppl. 118, pp. 118-121 (1986).
Wallmark, et al., "The Relationship Between Gastric Acid Secretion and Gastric $H^+$, $K^+$-ATPase Activity", Journal of Biological Chemistry, vol. 260, No. 25, pp. 13681-13684 (Nov. 5, 1985).
Wallmark, Bjorn, "Mechanism of Action of Omeprazole", Scand. J. Gastroenterology, vol. 21, Suppl. 118, pp. 11-16 (1986).
Wallmark, et al., "Mechanism of Inhibition of $H^{+-K+}$-ATPase by Omeprazole", Scand. J. Gastroenterology, vol. 21, Suppl. 118, pp. 59-60 (1986).
Wallmark, et al., Mechanism of Action of Omeprazole:, ISI Atlas of Science: Pharmacology, vol. 1, pp. 158-161 (1987).
Wilson, et al., "The Effect of Omeprazole on Acid and Pepsin Secretion in Duodenal Ulcer Patients", Scand. J. Gastroenterology, vol. 21, Suppl. 118, pp. 147-149 (1986).
Yeomans, et al., "Morning or Evening Dosing with Low-Dose Omeprazole: Effects on 24-Hour Gastric Acidity Profiles in Duodenal Ulcer Patients", Scand. J. Gastroenterology, vol. 21, Suppl. 118, pp. 152-153 (1986).
Zegerid Product Information, Feb. 2006.
Jun. 16, 2008 Par's Objection and Responses to Curators of the University of Missouri's 1st Set of Requests for Production of Documents, Case No. 07-551-GMS (D. Del.).
Jun. 23, 2008 Reponses and Objections of Tap Pharmaceutical Products Inc. to Defendant's Subpoena, Case Nos. 07-551-GMS and 07-827-GMS (D. Del.).
Jun. 26, 2008 Final Joint Claim Construction Chart, Case No. 07-551-GMS (D. Del.).
Jul. 9, 2008 Santarus' Responses to Par Pharmaceutical First Set of Interrogatories, Case No. 07-551-GMS (D. Del.).
Aug. 22, 2008 Defendant Par Pharmaceutical, Inc.'s Opening Claim Construction Brief Regarding U.S. Patent Nos. 6,489,346; 6,699,885; and 6,645,988, Case No. 07-551-GMS (D. Del.).
Aug. 26, 2008 Plaintiff's Opening Claim Construction Brief, Case No. 07-551-GMS (D. Del.).
Sep. 22, 2008 Defendant's Answering Brief Regarding Claim Construction, Case No. 07-551-GMS (D. Del.).
Sep. 22, 2008 Declaration of Steven J. Fineman, Case No. 07-551-GMS (D. Del.).
Sep. 22, 2008 Plaintiff's Answering Brief Regarding Claim Construction, Case No. 07-551-GMS (D. Del.).
DE 19752843 A1—Dietrich, et al., Jul. 1, 1999 (English Abstract).
ES 2024993 AF—Palomo Coll, Mar. 1, 1992 (English Abstract).
JP 02022225 A—Aoki, et al., Jan. 25, 1990 (English Abstract).
JP 03034967 A—Konishi, et al., Feb. 14, 1991 (English Abstract).
JP 03048680 A—Kawakita, et al., Mar. 1, 1991 (English Abstract).
JP 03052887 A—Kawakita, et al., Mar. 7, 1991 (English Abstract).
JP 03163018 A—Makino, et al., Jul. 15, 1991 (English Abstract).
JP 05117268 A—Kawakita, et al., May 14, 1993 (English Abstract).
JP 05194224 A—Oishi, et al., Aug. 3, 1993 (English Abstract).
JP 05194225 A—Oishi, et al., Aug. 3, 1993 (English Abstract).
JP 05255088 A—Oishi, et al., Sep. 17, 1992 (English Abstract).
JP 05294831 A—Kutsuto, et al., Nov. 9, 2003 (English Abstract).
JP 06092853 A—Nakanishi, et al., Apr. 5, 1994 (English Abstract).
JP 06100449 A—Kawakita, et al., Apr. 12, 1994 (English Abstract).
JP 07033659 A—Oishi, et al., Feb. 3, 2005 (English Abstract).
JP 09087110 A—Hidaka, et al., Mar. 31, 1997 (English Abstract).
JP 10017470 A—Hirayama, et al., Jan. 20, 1998 (English Abstract).
JP 10017471 A—Hirayama, et al., Jan. 20, 1998 (English Abstract).
JP 2000212180 A—Sano, et al., Aug. 2, 2000 (English Abstract).
JP 2000355540 A—Ukai, et al., Dec. 26, 2000 (English Abstract).
JP 45039541 B, Dec. 12, 1970 (English Abstract).
JP 45039543 B, Dec. 12, 1970 (English Abstract).
JP 46009580 B, Mar. 11, 1971 (English Abstract).
JP 46009581 B, Mar. 11, 1971 (English Abstract).
JP 48103567 A, Dec. 25, 1973 (English Abstract).
JP 49005967 A, Jan. 19, 1974 (English Abstract).
JP 49013172 A, Feb. 5, 1974 (English Abstract).
JP 49020173 A, Feb. 22, 1974 (English Abstract).
JP 49020174 A, Feb. 22, 1974 (English Abstract).
JP 49041198 B, Apr. 17, 1974 (English Abstract).
JP 49093537 A, Sep. 5, 1974 (English Abstract).
JP 49095997 A, Sep. 11, 1974 (English Abstract).
JP 50052065 A, May 9, 1975 (English Abstract).
JP 50112373 A, Sep. 3, 1975 (English Abstract).
JP 50142565 A, Nov. 17, 1975 (English Abstract).
JP 51016669 A, Feb. 10, 1976 (English Abstract).
JP 51131875 A, Nov. 16, 1976 (English Abstract).
JP 52005769 A, Jan. 17, 1977 (English Abstract).
JP 52014776 A, Feb. 3, 1977 (English Abstract).
JP 52097978 A, Aug. 1, 1977 (English Abstract).
JP 52102416 A, Aug. 27, 1977 (English Abstract).
JP 53059675 A, May 29, 1978 (English Abstract).
JP 55019211 A, Feb. 9, 1980 (English Abstract).
JP 56061311 A, May 26, 1981 (English Abstract).
JP 59095997 A, Jun. 2, 1984 (English Abstract).
JP 61221117 A, Oct. 1, 1986 (English Abstract).
JP 62145083 A—Matsuo, et al., Jun. 29, 1987 (English Abstract).
JP 62258316 A, Nov. 10, 1987 (English Abstract).
JP 62258320 A, Nov. 10, 1987 (English Abstract).
JP 62277322 A, Dec. 2, 1987 (English Abstract).
JP 622283964 A, Dec. 9, 1987 (English Abstract).
KR 9603605 B—Jung, et al., Mar. 20, 1996 (English Abstract).
KR 9611238 B—Yu, et al., Aug. 21, 1996 (English Abstract).
KR 9611390 B—Kim, et al., Aug. 22, 1996 (English Abstract).
Adams, et al., "Comments of the Report of Association of Omeprazole with DNA by Phillips, et al.,", Mutagensis, vol. 7, No. 5, pp. 395-396 (Sep. 1992).
Aihara, et al., "Pharmacological Control of Gastric Acid Secretion for the Treatment of Acid-Related Peptic Disease: Past, Present, and Future", Pharmacology & Therapeutics, vol. 98, pp. 109-127 (2003).
Al-Assi, et al., "Treatment of Heliocobacter Pylori Infection with Omeprazole-Amoxicillin Combination Therapy Versus Ranitidine/Sodium Bicarbonate-Amoxicillin", The American Journal of Gastroenterology, vol. 90, No. 9, pp. 1411-1414 (Sep. 1995).
Andersson, et al., "Pharmacokinetics of [14C] Omeprazole in Patients with Liver Cirrhosis", Clin. Pharmacokinet., vol. 24, No. 1, pp. 71-78 (1993).
Andersson, et al., "Pharmacokinetics and Bioavailability of Omerprazole After Single and Repeated Oral Administration in Healthy Subjects", British Journal of Clinical Pharmacology, vol. 29, pp. 557-563 (1990).

(56) References Cited

OTHER PUBLICATIONS

Andersson, "Pharmacokinetics, Metabolism, and Interactions of Acid Pump Inhibitors: Focus on Omeprazole, Lansoprazole and Pantoprazole", Clinical Pharmacokinetics, vol. 31, No. 1, pp. 9-28 (1996).
Andersson, et al., "Pharmacokinetics of Various Single Intravenous and Oral Doses of Omeprazole", European Journal of Clinical Pharmacology, vol. 39, pp. 195-197 (1990).
Andersson, et al., "Pharmacokinetic Studies with Esomeprazole, the (S)-Isomer of Omeprazole", Clinical Pharmacokinetics, vol. 40, No. 6, pp. 411-426 (2001).
Arvidsson, et al., "Peak Distortion in the Column Liquid Chromatographic Determination of Omeprazole Dissolved in Borax Buffer", Journal of Chromatography, vol. 586, pp. 271-276 (1991).
Balaban, at al., "Nasogastric Omeprazole: Effects on Gastric pH in Critically Ill Patients", The American Journal of Gastroenterology, vol. 92, No. 1, pp. 79-83 (1997).
Ballard, et al., "Bioequivalence Between Lansoprazole Sachet for Suspension and Intact Capsule", Gastroenterology, vol. 120, No. 5, Supp. 1, p. A-245 (Apr. 2001).
Ballesteros, et al., "Bolus or Intravenous Infusion of Ranitidine: Effects on Gastric pH and Acid Secretion", Annals of Internal Medicine, vol. 112, pp. 334-339 (Mar. 1, 1990).
Barie, et al., "Therapeutic Use of Omeprazole for Refractory Stress-Induced Gastric Mucosal Hemorrhage", Critical Care Medicine, vol. 20, No. 6, pp. 899-901 (1992).
Beekman, "Preparation and Properties of New Gastric Antacids I", Journal of the American Pharmaceutical Association, vol. 49, pp. 191-200 (1960).
Bennett & Dickson, eds., "AMA Drug Evaluations", 2nd Ed., pp. 773-827 (1973).
Blum, "Therapeutic Approach to Ulcer Healing", The American Journal of Medicine, vol. 79, Supp. 2C, pp. 8-14 (Aug. 30, 1985).
Bone, "Let's Agree on Terminology: Definitions of Sepsis," Critical Care Medicine, vol. 19, No. 7, pp. 973-976 (Jul. 1991).
Borella, et al., Abstract for "Gastric Antisecretory and Antiulcer/Cyptoprotective Effects of 2-Cyano-3-(Ethylthio-3-Methylthio)-2-Propenoic Acid Methyl Ester", Wyeth-Ayerst Res. Inc. (1989).
Borrero, et al., "Antacids v. Sucralfate in Preventing Acute Gastrointestinal Tract Bleeding in Abdominal Aortic Surgery", Arch. Surg., vol. 121, pp. 810-812 (Jul. 1986).
Brunton, "Agents for Control of Gastric Acidity and Treatment of Peptic Ulcers", The Pharmacologic Basis of Therapeutics, Ch. 37, pp. 897-913 (1990).
Cantu, et al., "Central Nervous System Reactions to Histamine-2 Receptor Blockers", Annals of Internal Medicine, vol. 114, No. 12, pp. 1027-1034 (Jun. 15, 1991).
Caos, et al., "Rabeprazole for the Prevention of Pathologic and Symptomatic Relapse of Erosive or Ulcerative Gastroesophageal Reflux Disease", The American Journal of Gastroenterology, vol. 95, No. 11, pp. 3081-3088 (2000).
Carroll, et al., Abstract of "Nasogastric Administration of Omeprazole for Control of Gastric pH", 10th World Congresses of Gastroenterology, Abstracts II: Poster Presentations, (Oct. 2-7, 1994).
Cederberg, et al., "Omeprazole: Pharmacokinetics and Metabolism in Man", Scandanavian Journal of Gastroenterology, vol. 24, Supp. 166, pp. 33-40 (1989).
Cederberg, et al., "Effect of Once Daily Intravenous and Oral Omeprazole on 24-Hour Intragastric Acidity in Healthy Subjects", Scandanavian Journal of Gastroenterology, vol. 28, pp. 179-184 (1993).
Ching, et al., "Antacids—Indications and Limitations", Drugs, vol. 47, No. 2, pp. 305-317 (Feb. 1994).
Cioffi, et al., "Comparison of Acid Neutralizing and Non-Acid Neutralizing Stress Ulcer Prophylaxis in Thermally Injured Patients", The Journal of Trauma, vol. 36, No. 4, pp. 541-547, (Apr. 1994).
Cook, et al., "Nosocomial Pneumonia and the Role of Gastric pH", Chest, vol. 100, No. 1, pp. 7-13 (1991).
Cook, et al., "Risk Factors for Gastrointestinal Bleeding in Critically Ill Patients", The New England Journal of Medicine, vol. 330, No. 6, pp. 377-381 (Feb. 10, 1994).
Cook, et al., "Stress Ulcer Prophylaxis in the Critically Ill: A Meta-Analysis", The American Journal of Medicine, vol. 91, pp. 519-527 (Nov. 1991).
Grill, et al., "Upper Gastrointestinal Tract Bleeding in Critically Ill Pediatric Patients", Pharmacotherapy, vol. 19, No. 2, pp. 162-180 (1999).
Czaja, et al., "Acute Gastroduodenal Disease After Thermal Injury", The New England Journal of Medicine, vol. 291, No. 18, pp. 925-929 (Oct. 31, 1974).
Deakin, et al., "Are We Making Progress in the Drug Treatment of Oesophageal Disease?", Journal of Clinical Pharmacy and Therapeutics, vol. 13, pp. 365-374 (1988).
Di Iorio, et al., "Aluminum and Phosphorus Urinary Excretion After Modifying Gastric Acid Secretion in Normal Subjects", Trace Elements and Electrolytes, vol. 13, No. 1, pp. 47-49 (1996).
Di Iorio, et al., "Aluminum and Phosphorus Urinary Excretion After Modifying Gastric Acid Secretion in Chronic Renal Failure", Trace Elements and Electrolytes, vol. 13, No. 2, pp. 96-101 (1996).
Digiacinto, et al., "Stability of Suspension Formulations of Lansoprazole and Omeprazole Stored in Amber-Colored Plastic Oral Syringes", The Annals of Pharmacotherapy, vol. 34, pp. 600-605 (May 2000).
Doan, et al., "Comparative Pharmacokinetics and Pharmacodynamics of Lansoprazole Oral Capsules and Suspension in Healthy Subjects", American Journal of Health-System Pharmacists, vol. 58, pp. 1512-1519 (Aug. 5, 2001).
Dobkin, et al., "Does pH Paper Accurately Reflect Gastric pH?", Critical Care Medicine, vol. 18, No. 9, pp. 985-988 (Sep. 1990).
Driks, et al., "Noscomial Pneumonia in Intubated Patients Given Sucralfate as Compared With Antacids or Histamine Type 2 Blockers", The New England Journal of Medicine, vol. 317, No. 22, pp. 1376-1382 (Nov. 26, 1987).
Eisenberg, et al., "Prospective Trial Comparing a Combination pH Probe-Nasogastric Tube with Aspirated Gastric pH in Intensive Care Unit Patients", Critical Care Medicine, vol. 18, No. 10, pp. 1092-1095 (1990).
Ekpe, et al., "Effect of Various Salts on the Stability of Lansoprazole, Omeprazole and Pantaprazole as Determined by High-Performance Liquid Chromatography", Drug Development and Industrial Pharmacy, vol. 25, No. 9, pp. 1057-1065 (1999).
Elliott, "Nasogastric Administration of Omeprazole", The Australian Journal of Hospital Pharmacists, vol. 28, No. 3 (Feb. 1998).
Fabian, et al., "Pneumonia and Stress Ulceration in Severely Injured Patients", Archives of Surgery, vol. 128, pp. 185-191 (Feb. 1993).
Fellenius, et al., "Substituted Benzimidazoles Inhibit Gastric Acid Secretion by Blocking ($H^+/K^+$)ATPase", Nature, vol. 290, pp. 159-161 (Mar. 12, 1981).
Ferron, et al., "Oral Bioavailiability of Pantoprazole Suspended in Sodium Bicarbonate Solution", American Journal of Health-System Pharmacists, vol. 60, pp. 1324-1328 (Jul. 1, 2003).
Fiddian-Green, et al., "Predictive Value of Intramural pH and Other Risk Factors for Massive Bleeding from Stress Ulceration", Gastroenterology, vol. 85, No. 3, pp. 613-620 (Sep. 1983).
Fitton, et al., "Pantoprazole, A Review of its Pharmacological Properties and Therapeutic Use in Acid-Related Disorders", Drugs, vol. 51, No. 3, pp. 460-482 (Mar. 1996).
Fryklund, et al., "Function and Structure of Parietal Cells After $H^+/K^+$-ATPase Blockade", American Journal of Physiology, vol. 254, pp. G399-G407 (1988).
Fuchs, "Antacids, Their Function, Formulation and Evaluation", Drug and Cosmetic Industry, vol. 64, No. 6, pp. 692-773 (Jun. 1949).
Gafter, et al., "Thrombocytopenia Associated with Hypersensitivity to Ranitidine: Possible Cross-Reactivity with Cimetidine", The American Journal of Gastroenterology, vol. 84, No. 5, pp. 560-562 (May 1989).
Garner, et al., "CDC Definitions for Nosocomial Infections, 1988", American Journal of Infection Control, vol. 16, No. 3, pp. 128-140 (Jun. 1988).

(56) References Cited

OTHER PUBLICATIONS

Garnett, "Efficacy, Safety and Cost Issues in Managing Patients with Gastroesophageal Reflux Disease", American Journal of Hospital Pharmacists, vol. 50, Supp. 1, pp. 511-518 (Apr. 1993).
Goodman, et al., "Agents for Control of Gastric Acidity and Treatment of Peptic Ulcers", The Pharmacological Basis of Therapeutics, Chapter 37, pp. 907-909, 1768 (9th ed. 1996).
Gray, et al., "Influence of Insulin Antibodies on Pharmacokinetics and Bioavailability of Recombinant Human and Highly Purified Beef Insulins in Insulin Dependent Diabetics", British Medical Journal, vol. 290, pp. 1687-1691 (Jun. 8, 1985).
Hardy, et al., "Inhibition of Gastric Secretion by Omeprazole and Efficiency of Calcium Carbonate on the Control of Hyperphosphatemia in Patients on Chronic Hemodialysis", Artificial Organs, vol. 22, No. 7, pp. 569-573 (1998).
Hatlebakk, et al., "Lansoprazole Capsules and Amoxicillin Oral Suspension in the Treatment of Peptic Ulcer Disease", Scandanavian Journal of Gastroenterology, vol. 30, pp. 1053-1057 (1995).
Heath, et al., "Intragastric pH Measurement Using a Novel Disposable Sensor", Intensive Care Medicine, vol. 14, pp. 232-235 (1988).
Hixon, et al., "Current Trends in the Pharmacotherapy for Gastroesophageal Reflux Disease", Archives of Internal Medicine, vol. 152, pp. 717-723 (Apr. 1992).
Hixon, et al., "Current Trends in the Pharmacotherapy for Peptic Ulcer Disease", Archives of Internal Medicine, vol. 152, pp. 726-732 (Apr. 1992).
Holbert, et al., "A Study of Antacid Buffers: I. The Time Factor in Neutralization of Gastric Acidity", Journal of the American Pharmaceutical Association, vol. 36, pp. 149-151 (1947).
Holt, et al., "Omeprazole, Overview and Opinion", Digestive Diseases and Sciences, vol. 36, No. 4, pp. 385-393 (Apr. 1991).
Horn, "The Proton-Pump Inhibitors: Similarities and Differences", Clinical Therapeutics, vol. 22, No. 3, pp. 266-280 (2000).
Horowitz, et al., "The Effect of Omeprazole on Gastric Emptying in Patients with Duodenal Ulcer Disease", British Journal of Clinical Pharmacology, vol. 18, pp. 791-794 (1984).
Howden, et al., "Oral Pharmacokinetics of Omeprazole", European Journal of Clinical Pharmacology, vol. 26, pp. 641-643 (1984).
Huber, et al., "Pharmacokinetics of Pantoprazole in Man", International Journal of Clinical Pharmacology and Therapeutics, vol. 34, No. 5, pp. 185-194 (1996).
Humphries, et al., "Review Article: Drug Interactions with Agents Used to Treat Acid-Related Diseases", Ailment Pharmacol. Ther., vol. 13, Supp. 3, pp. 18-26 (1999).
Jungnickel, "Pantoprazole: A New Proton Pump Inhibitor", Clinical Therapeutics, vol. 22, No. 11, pp. 1268-1293 (2000).
Karol, et al., "Pharmacokinetics of Lansoprazole in Hemodialysis Patients", Journal of Clinical Pharmacology, vol. 35, pp. 815-820 (1995).
Kihira, et al., "Endoscopic Topical Therapy for the Treatment of Heliobacter Pylori Infection", Journal of Gastroenterology, vol. 31, Supp. IX, pp. 65-68 (1996).
Kiilerich, et al., "Effect of Intravenous Infusion of Omeprazole and Ranitidine on Twenty-Four-Hour Intragastric pH in Patients with a History of Duodenal Ulcer", Digestion, vol. 56, pp. 25-30 (1995).
Korponay-Szabo, et al., Abstract of "High Acid Buffering Capacity of Protein Hydrolysate Infant Formulas", Journal of Pediatric Gastrenterology and Nutrition, vol. 31, Supp. 2, Abstract 956 (Aug. 9, 2000).
Kromer, et al., "Similarities and Differences in the Properties of Substituted Benzimidazoles: A Comparison Between Pantoprazole and Related Compounds", Digestion, vol. 56, pp. 443-454 (1995).
Kromer, et al., "Differences in pH-Dependent Activation Rates of Substituted Benzimidazoles and Biological in Vitro Correlates", Pharmacology, vol. 56, pp. 57-70 (1998).
Laggner, et al., "Prevention of Upper Gastrointestinal Bleeding in Long-Term Ventilated Patients", The American Journal of Medicine, vol. 86, Supp. 6A, pp. 81-84 (Jun. 9, 1989).
Landahl, et al., "Pharmacokinetic Study of Omeprazole in Elderly Healthy Volunteers", Clinical Pharmacokinetics, vol. 23, No. 6, pp. 469-476 (1992).
Larson, et al., "Gastric Response to Severe Head Injury", The American Journal of Surgery, vol. 147, pp. 97-105 (Jan. 1984).
Larson, et al., "Bioavailability and Efficacy of Omeprazole Given Orally and by Nasogastric Tube", Digestive Diseases and Sciences, vol. 41, No. 3, pp. 475-479 (Mar. 1996).
Larsson, et al., "Gastric Acid Antisecretory Effect of Two Different Dosage Forms of Omeprazole During Prolonged Oral Treatment in the Gastric Fistula Dog", Scandanavian Journal of Gastroenterology, vol. 23, No. 8, pp. 1013-1019 (1988).
Lasky, et al., "A Prospective Study of Omeprazole Suspension to Prevent Clinically Significant Gastrointestinal Bleeding from Stress Ulcers in Mechanically Ventilated Trauma Patients", The Journal of Trauma: Injury, Infection and Critical Care, vol. 44, No. 3, pp. 527-533 (Mar. 1998).
Ley, et al., "Bioavailability of a Crushed Pantoprazole Tablet After Buffering with Sodium Hydrogencarbonate or Magaldrate Relative to the Intact Enteric Coated Pantoprazole Tablet", Methods and Findings in Experimental and Clinical Pharmacology, vol. 23, No. 1, pp. 41-45 (2001).
Lin, et al., "Evaluation of Buffering Capacity and Acid Neutralizing pH Time Profile of Antacids", J. Formos Med. Assoc., vol. 97, No. 10, pp. 704-710 (1998).
Lind, et al., "Inhibition of Basal and Betazole- and Sham-Feeding-Induced Acid Secretion by Omeprazole in Man", Scandanavian Journal of Gastroenterology, vol. 21, pp. 1004-1010 (1986).
Lockhart, et al., Abstract of "A Lansoprazole Suspension Formulation as an Alternative to Capsules for Oral Administration", Digestion, vol. 59, Supp. 3, p. 226, Abstract ExhA2074 (1998).
Londong, et al., "Dose-Response Study of Omeprazole on Meal-Stimulated Gastric Acid Secretion and Gastrin Release", Gastroenterology, vol. 85, No. 6, pp. 1373-1378 (1983).
Maconi, et al., "Prolonging Proton Pump Inhibitor-Based Anti-Helicobacter Pylori Treatment from One to Two Weeks in Duodenal Ulcer: Is it Worthwhile'?", Digest Liver Disease, vol. 32, pp. 275-280 (2000).
Marrone, et al., "Pathogenesis, Diagnosis and Treatment of Acute Gastric Mucosa Lesions", Clinics in Gastroenterology, vol. 13, No. 2, pp. 635-650 (May 1984).
Martin, Physical Pharmacy—Physical Chemical Principles in the Pharmaceutical Sciences, 4th Ed., "Buffered and Isotonic Solutions", pp. 169-189 (1993).
Martin, et al., "Continuous Intravenous Cimetidine Decreases Stress-Related Upper Gastrointestinal Hemorrhage Without Promoting Pneumonia", Critical Care Medicine, vol. 21, No. 1, pp. 19-30 (1993).
Martin, et al., "Stress Ulcers and Organ Failure in Intubated Patients in Surgical Intensive Care Units", Annals of Surgery, vol. 215, No. 4, pp. 332-337 (Apr. 1992).
Martindale, The Extra Pharmacopeia, 29th Ed., pp. 1025-1027 (1989).
Maxwell, et al., Abstract of "Control of Gastric pH in a Critical Care Unit: Physician Behavior and Pharmacologic Effectiveness", American Review of Respiratory Disease, vol. 143, No. 4, Part 2, p. A482 (Apr. 1991).
McAndrews, et al., "Omeprazole and Lansprazole Suspensions for Nasogastric Administration", American Journal of Health-System Pharmacists, vol. 56, p. 81 (Jan. 1, 1999).
McTavish, et al., "Omeprazole—An Updated Review of its Pharmacology and Therapeutic Use in Acid-Related Disorders", Drugs, vol. 42, No. 1, pp. 138-170 (1991).
Meiners, et al., "Evaluation of Various Techniques to Monitor Intragastric pH", Archives of Surgery, vol. 117, pp. 288-291 (Mar. 1982).
Metzler, Presentation of "Advances in the Use of PPI's from Efficacy to Effectiveness", Overview of Omeprazole Suspension (1999).
Mohiuddin, et al., "Effective Gastric Acid Suppression After Oral Administration of Enteric-Coated Omeprazle Granules", Digestive Diseases and Sciences, vol. 42, No. 4, pp. 715-719 (Apr. 1997).

(56) References Cited

OTHER PUBLICATIONS

Nakagawa, et al., "Phase I Study of Lansoprazole (AG-1749) Anti-ulcer Agent—Tablet Form", Journal of Therapeutics & Medicines, vol. 7, No. 1, pp. 33-50 (1991).
Nakamura, et al, "Effect of Combined Administration of Lansoprazole and Sofalcone on Microvascular and Connective Tissue Regeneration After Ethanol-Induced Gastric Mucosal Damage", Journal of Clinical Gastroenterology, vol. 27, Supp. 1, pp. S170-S177 (1998).
Naunton, et al., "Overuse of Proton Pump Inhibitors", Journal of Clinical Pharmacy and Therapeutics, vol. 25, pp. 333-340 (2000).
Oh, et al., "Electrolyte and Acid-Based Disorders", The Pharmacologic Approach to the Critically Ill Patient, Ch. 57, pp. 957-968 (1994).
Oosterhuis, et al., "Omeprazole: Pharmacology, Pharmacokinetics and Interactions", Digestion, vol. 44, Supp. 1, pp. 9-17 (1989).
Osler, et al., "Effect of Omeprazole on the Phosphate-Binding Capacity of Calcium Carbonate", Nephron, vol. 69, pp. 89-90 (1995).
Ostro, et al., "Control of Gastric pH with Cimetidine: Boluses Versus Primed Infusions", Gastroenterology, vol. 89, No. 3, pp. 532-537 (Sep. 1985).
Paul, et al., Abstract of "Pantoprazole Bicarbonate Suspension (PBS) Provides Oral Bioavailability Comparable to Tablet", Critical Care Medicine, Abstract 563/T151 (Feb. 10-14, 2001).
Peura, et al., "Cimetidine for Prevention and Treatment of Gastroduodenal Mucosal Lesions in Patients in an Intensive Care Unit", Annals of Internal Medicine, vol. 103, No. 2, pp. 173-177 (Aug. 1985).
Phillips, Declaration of, with Exhibits A-G filed in U.S. Appl. No. 90/007,686, filed Sep. 20, 2006.
Phillips, Poster Presented at the Society for Critical Care Medicine Annual Meeting Relating to SOS (Jan. 1994).
Phillips, Presentation of "Stress-Related Mucosal Damage Optimizing Drug Therapy in the 1990's", The University of Missouri Surgical Society (Jun. 1994).
Phillips, Presentation of "Update on Acid-Related Disorders—Optimizing Pharmacotherapy for the 1990's", A Model for Optimizing Pharmacotherapy (1996).
Phillips, Presentation of "Stress-Related Mucosal Damage—Optimizing Drug Therapy", Prophylaxis of Stress Ulcers (1997).
Phillips, Presentation of "From Efficacy to Effectiveness Alternative Dosing of PPI's", Overview of Omeprazole Suspension (Aug. 1998).
Phillips, Presentation of "Simplified Omeprazole Suspension (SOS)" (1998).
Phillips, Presentation of "Overview of Omeprazole Suspension: Problems with Administering Granules" (1999/2000).
Phillips, Presentation of "Pharmacotherapy Related Outcomes Group Researching Effective Stress Ulcer Strategies", Overview of Omeprazole Suspension (2000).
Phillips, Presentation of "Stress Ulcer Prophylaxis in the 21st Century", Overview of Omeprazole Suspension (2001).
Phillips, Poster Presentation of "Simplified Omeprazole Solution (SOS)—Pharmacokinetic/Pharmacodynamic Study in Patients at Risk for Stress Related Mucosal Damage (SRMD)", Project #5122.
Phillips, Presentation of "Advances in the Use of PPI's From Efficacy to Effectiveness", Overview of Omeprazole Suspension (1999).
Phillips, et al., Abstract of "The Stability of Simplified Lansoprazole Suspension (SLS)", Gastroenterology, vol. 116, No. 4, Abstract G0382 (Apr. 1999).
Phillips, et al., Abstract of "Use of Flavored Lansoprazole or Omeprazole Suspensions in Pediatric Gerd", Supplement to Gastroenterology, vol. 118, No. 4, Supp. 2, Abstract 5904 (Apr. 2000).
Phillips, et al., Abstract of "A Randomized, Crossover Study of Duodenal or Jejunal Compared to Nasogastric Administration of Omeprazole Suspension in Critically Ill Patients", Pharmacotherapy, vol. 20, No. 10, p. 1237, Abstract 43 (Oct. 2000).
Phillips, et al., Abstract of "Simplified Omeprazole Solution for the Prophylaxis of Stress-Related Mucosal Damage in Critically Ill Patients", Critical Care Medicine, vol. 22, No. 1, p. A53 (Jan. 1994).
Phillips, et al., "A Prospective Study of Simplified Omeprazole Suspension for the Prophylaxis of Stress-Related Mucosal Damage", Critical Care Medicine, vol. 24, No. 11, pp. 1793-1800 (1996).
Phillips, et al., Abstract of "The Stability of Simplified Omeprazole Suspension (SOS)", Critical Care Medicine, vol. 26, No. 1 (Supp.), p. A101, Abstract 221 (1998).
Phillips, et al., Abstract of "A Multicenter, Prospective, Randomized Clinical Trial of Continuous Infusion I.V. Ranitidine vs. Omeprazole Suspension in the Prophylaxis of Stress Ulcers", Critical Care Medicine, vol. 26, No. 1 (Supp.), p. A101, Abstract 222 (1998).
Phillips, et al., Abstract of "Flavored Lansoprazole Suspension in Pediatric Gerd", Journal of Pediatric Gastroenterology and Nutrition, vol. 31, Supp. 2, p. S181, Abstract 707 (Aug. 2000).
Phillips, et al., "Interaction of Omperazole with DNA in Rat Tissues", Mutagenesis, vol. 7, No. 4, pp. 277-283 (1992).
Phillips, et al., "A Randomized, Pharmacokinetic and Pharmacodynamic, Cross-Over Study of Duodenal or Jejunal Administration Compared to Nasogastric Administration of Omeprazole Suspension in Patients at Risk for Stress Ulcers", The American Journal of Gastroenterology, vol. 96, No. 2, pp. 367-372 (2001).
Pickworth, et al., "Occurrence of Nosocomial Pneumonia in Mechanically Ventilated Trauma Patients: A Comparison of Sucralfate and Ranitidine", Critical Care Medicine, vol. 21, No. 12, pp. 1856-1862 (Dec. 1993).
Pilbrant, et al., "Development of an Oral Formulation of Omeprazole", Scandanavian Journal of Gastroenterology, vol. 20, Supp. 108, pp. 113-120 (1985).
Pilbrant, "Principles for Development of Antacids", Scandanavian Journal of Gastroenterology, vol. 75, pp. 32-37 (1982).
Pipkin, et a., "Onset of Action of Antisecretory Drugs: Beneficial Effects of a Rapid Increase in Intragastric pH in Acid Reflux Disease", Scandanavian Journal of Gastroenterology, vol. 34, Supp. 230, pp. 3-8 (1999).
Prichard, et al., "Omeprazole: A Study of Its Inhibition of Gastric pH and Oral Pharmacokinetics After Morning or Evening Dosage", Gastroenterology, vol. 88, No. 1, Part 1, pp. 64-69 (Jan. 1985).
Priebe, et al., "Methods of Prophylaxis in Stress Ulcer Disease", World Journal of Surgery, vol. 5, No. 2, pp. 233-233 (Mar. 1981).
Quercia, et al., "Stability of Omeprazole in an Extemporaneously Prepared Oral Liquid", American Journal of Health-System Pharmacists, vol. 54, pp. 1833-1836 (Aug. 15, 1997).
Regardh, et al., "Pharmacokinetics and Metabolism of Omeprazole in Animals and Man—An Overview", Scandanavian Journal of Gastrenterology, vol. 20, Supp. 108, pp. 79-94 (1985).
Regardh, et al., "The Pharmacokinetics of Omeprazole in Humans—A Study of Single Intravenous and Oral Doses", Therapeutic Drug Monitoring, vol. 12, No. 2, pp. 163-172 (1990).
Rodrigo, et al., "Therapeutic Approach to Peptic Ulcer Relapse", Meth. Find Exp. Clin. Pharmacol., vol. 11, Supp. 1, pp. 131-135 (1989).
Roy, et al., "Zollinger-Ellison Syndrome—Clinical Presentation in 261 Patients", Medicine, vol. 79, No. 6, pp. 379-411, (2000).
Ryan, et al., "Nosocomial Pneumonia During Stress Ulcer Prophylaxis with Cimetidine and Sucralfate", Archives of Surgery, vol. 128, pp. 1353-1357 (Dec. 1993).
Sax, "Clinically Important Adverse Effects and Drug Interactions with H2-Receptor Antagonists: An Update", Pharmacotherapy, vol. 7, No. 6, Part 2, pp. 110S-115S (1987).
Schepp, "Stress Ulcer Prophylaxis: Still a Valid Option in the 1990s?", Digestion, vol. 54, pp. 189-199 (1993).
Schmassmann, et al., "Antacid Provides Better Restoration of Glandular Structures Within the Gastric Ulcer Scar Than Omeprazole", Gut, vol. 35, pp. 896-904 (1994).
Schmassmann, et al., "Antacids in Experimental Gastric Ulcer Healing: Pharmacokinetics of Aluminum and Quality of Healing", European Journal of Gastroenterology & Hepatology, vol. 5, Supp. 3, pp. S111-S116 (1993).
Schuster, "Stress Ulcer Prophylaxis: In Whom? With What?", Critical Care Medicine, vol. 21, No. 1, pp. 4-6 (Jan. 1993).
Sechet, et al., "Role of the Time of Administration of Calcium Carbonate in the Control of Hyperphophatemia in Patients on Maintenance Dialysis", Nephrologie, vol. 20, pp. 209-220 (1999).

(56) References Cited

OTHER PUBLICATIONS

Sechet, et al., "Inhibition of Gastric Secretion by Omeprazole in Efficacy of Calcium Carbonate in the Control of Hyperphosphatemia in Patients on Maintenance Dialysis", Nephrologie, vol. 20, pp. 213-216 (1999).
Sharma, et al., "The Pharmacodynamics of Lansoprazole Administered Via Gastrostomy as Intact, Non-Encopsulated Granules", Ailment Pharmacol. Ther., vol. 12, pp. 1171-1174 (1998).
Sharma, et al., "The Effects on Intragastric Acidity of Per-Gastrostomy Administration of an Alkaline Suspension of Omeprazole", Ailment Pharmacol. Ther., vol. 13, pp. 1091-1095 (1999).
Sharma, et al., "Oral Pharmacokinetics of Omeprazole and Lansoprazole After Single and Repeated Doses as Intact Capsules or as Suspensions in Sodium Bicarbonate", Ailment. Pharmacol. Ther., vol. 14, pp. 887-892 (2000).
Sharma, "Comparison of 24-Hour Intragastric pH Using Four Liquid Formulations of Lansoprazole and Omeprazole", American Journal of Health-System Pharmacists, vol. 56, Supp. 4, pp. S18-S21 (Dec. 1, 1999).
Sharma, et al., Abstract of "Effect on 24-Hour Intragastric Acidity of Simplified Omeprazole Solution (SOS) Administered Via Gastrostomy", the American Journal of Gastroenterology, vol. 92, No. 9, p. 1625, Abstract 169 (1997).
Sharma, et al., "Simplified Lansoprazole Suspension—A Liquid Formulation of Lansoprazole—Effectively Suppress Intragastric Acidity When Administered Through a Gastrostomy", The American Journal of Gastroenterology, vol. 94, No. 7, pp. 1813-1817 (Jul. 1999).
Sharma, et al., Abstract of "Simplified Lansoprazole Suspension (SLS): A Proton Pump Inhibitor (PPI) in a Liquid Formulation That Works", The American Journal of Gastroenterology, vol. 93, No. 9, pp. 1647, Abstract 153 (Sep. 1998).
Shuman, et al., "Prophylactic Therapy for Stress Ulcer Bleeding: A Reappraisal", Annals of Internal Medicine, vol. 106, pp. 562-567 (1987).
Siepler, "A Dosage Alternative for H2—Receptor Antagonists—Constant Infusion", Clinical Therapeutics, vol. 8, Supp. A, pp. 24-33 (1986).
Siepler, et al., "Selecting Drug Therapy for Patients with Duodenal Ulcers", Clinical Pharmacy, vol. 9, pp. 463-467 (Jun. 1990).
Sih, et al., "Studies on ($H^+$-$K^+$)-ATPase Inhibitors of Gastric Acid Secretion. Prodrugs of 2-[(2-Pyridinylmethyl)Sulfinyl] Benzimidazole Proton-Pump Inhibitors", Journal of Medicinal Chemistry, vol. 34, No. 3, pp. 1049-1062 (1991).
Simms, et al., "Role of Gastric Colonization in the Development of Pneumonia in Critically Ill Trauma Patients: Results of a Prospective Randomized Trial", The Journal of Trauma, vol. 31, No. 4, pp. 531-536 (Apr. 1991).
Skillman, et al., "Respiratory Failure, Hypotension, Sepsis and Jaundice", American Journal of Surgery, vol. 117, pp. 523-530 (Apr. 1969).
Skillman, et al., "The Gastric Mucosal Barrier: Clinical and Experimental Studies in Critically Ill and Normal Man, and in the Rabbit", Annals of Surgery, vol. 172, No. 4, pp. 564-584 (Oct. 1970).
Tryba, "Risk of Acute Stress Bleeding and Nosocomial Pneumonia in Ventilated Intensive Care Patients: Sucralfate Versus Antacids", The American Journal of Medicine, vol. 83, Supp. 3B, pp. 117-124 (Sep. 28, 1987).
Tytgat, "Drug Therapy of Reflux Oesophagitis: An Update", Scandanavian Journal of Gastroenterology, vol. 24, Supp. 168, pp. 38-49 (1989).
Vial, et al., "Side Effects of Ranitidine", Drug Safety, vol. 6, No. 2, pp. 94-117 (1991).
Vincent, et al., Abstract of "Concurrent Administration of Omeprazole and Antacid Does Not Alter the Pharmacokinetics and Pharmacodynamics of Dofetilide in Healthy Subjects", Clinical Pharmacology & Therapeutics, vol. 59, No. 2, pp. 182, Abstract PII-93, (Feb. 1996).
Wade, Organic Chemistry, Prentice-Hall, Inc., Chapter 8, pp. 349-350 (1987).
Walan, "Pharmacological Agents for Peptic Ulcer Disease", Scandanavian Journal of Gastroenterology, vol. 19, No. 98, p. 1 (1984).
Watanabe, et al., "Pharmacokinetic Evaluation of Omeprazole Suspension Following Oral Administration in Rats: Effect of Neutralization of Gastric Acid", Acta Med. Okayama, vol. 50, No. 4, pp. 219-222 (Aug. 1996).
Whipple, et al., Abstract of "The Effect of Omeprazole/Sodium Bicarbonate Solution Administration on the Accuracy of Subsequent pH Measurements Through the Nasogastric Tube", Critical Care Medicine, vol. 23, No. 1 (Supp.), p. A69 (Jan. 1995) [Date stamped at Central DuPage Hospital on Jan. 10, 1995].
Whipple, et al., Abstract of "The Effect of Omeprazole/Sodium Bicarbonate Solution Administration on the Accuracy of Subsequent pH Measurements Through the Nasogastric Tube", Critical Care Medicine, vol. 23, No. 1 (Supp.), p. A69 (Jan. 1995) [Date stamped at FDA Medical Library on Jan. 6, 1995].
Whipple, et al., Abstact of "The Effect of Omeprazole/Sodium Bicarbonate Solution Administration on the Accuracy of Subsequent pH Measurements Through the Nasogastric Tube", Critical Care Medicine, vol. 23, No. 1 (Supp.), p. A69 (Jan. 1995) [Date stamped at Howard University Health Sciences Library on Jan. 13, 1995].
Whipple, et al., Abstact of "The Effect of Omeprazole/Sodium Bicarbonate Solution Administration on the Accuracy of Subsequent pH Measurements Through the Nasogastric Tube", Critical Care Medicine, vol. 23, No. 1 (Supp.), p. A69 (Jan. 1995).
Whipple, et al., Abstact of "The Effect of Omeprazole/Sodium Bicarbonate Solution Administration on the Accuracy of Subsequent pH Measurements Through the Nasogastric Tube", Critical Care Medicine, vol. 23, No. 1 (Supp.), p. A69 (Jan. 1985) [Although allegedly date stamped at St. Vincent's Hospital Medical Library on Jan. 3, 1995, interviews of library personnel revealed that this Supplement was not received until Jan. 9, 1995, as the Jan. 9, 1995 date is found in their computerized database.]
Whipple, et al., Abstact of "The Effect of Omeprazole/Sodium Bicarbonate Solution Administrationon the Accuracy of Subsequent pH Measurements Through the Nasogastric Tube", Critical Care Medicine, vol. 23, No. 1, Supp., p. A69 (Jan. 1995) [Date stamped at University of Illinois on Jan. 10, 1995].
Whipple, et al., Abstact of "The Effect of Omeprazole/Sodium Bicarbonate Solution Administration on the Accuracy of Subsequent pH Measurements Through the Nasogastric Tube", Critical Care Medicine, vol. 23, No. 1 (Supp.), p. A69 (Jan. 1995) [Date stamped at University of Missouri Health Sciences Library on Jan. 6, 1995].
Whipple, et al., Abstract of "The Effect of Omeprazole/Sodium Bicarbonate Solution Administration on the Accuracy of Subsequent pH Measurements Through the Nasogastric Tube", Critical Care Medicine, vol. 23, No. 1 (Supp.), p. A69 (Jan. 1995) [Date stamped at Walter Reed Army Medical Center Medical Library on Jan. 17, 1995].
Wilder-Smith, et al., "Tolerance During Dosing with $H_2$-Receptor Antagonists, An Overview", Scandanavian Journal of Gastroenterology, vol. 27, Supp. 193, pp. 14-19 (1992).
Yamakawa, et al., "Synthesis and Structure-Activity Relationships of Substituted 2-[(2-Imidazolylsulfinyl)Methyl] Anilines as a New Class of Gastric $H^+$/$K^+$-ATPase Inhibitors", Chem. Pharm. Bull., vol. 40, No. 3, pp. 675-682 (Mar. 1992).
Yusada, et al., "Antacids Have No Influence on the Pharmacokinetics of Rabeprazole, A New Proton Pump Inhibitor, in Healthy Volunteers", International Journal of Clinical Pharmacology and Therapeutics, vol. 37, No. 5, pp. 249-253 (1999).
Zinner, et al., "The Prevention of Gastrointestinal Tract Bleeding in Patients in an Intensive Care Unit", Surgery, Gynecology & Obstetrics, vol. 153, pp. 214-220 (Aug. 1981).
Dec. 20, 2001, Supplemental Information Disclosure Statement as filed with the U.S. Patent and Trademark Office for U.S. Appl. No. 09/481,207 (U.S. Patent No. 6,489,346).
Jun. 20, 1997, U.S. Patent 5,840,737 (U.S. Appl. No. 08/680,376)—Information Disclosure Statement Filed with the U.S. Patent and Trademark Office.

(56) References Cited

OTHER PUBLICATIONS

Feb. 28, 2001, U.S. Patent 6,489,346 (U.S. Appl. No. 09/481,207)—Information Disclosure Statement Filed with the U.S. Patent and Trademark Office.
Jul. 11, 2001, U.S. Patent 6,489,346 (U.S. Appl. No. 09/481,207)—Information Disclosure Statement Filed with the U.S. Patent and Trademark Office.
Dec. 21, 2001, U.S. Patent 6,849,346 (U.S. Appl. No. 09/481,207)—Information Disclosure Statement Filed with the U.S. Patent and Trademark Office.
Feb. 27, 2003, U.S. Patent 6,645,988 (U.S. Appl. No. 09/901,942)—Information Disclosure Statement Filed with the U.S. Patent and Trademark Office.
Jul. 25, 2003, U.S. Patent 6,699,885 (U.S. Appl. No. 10/054,350)—Information Disclosure Statement Filed with the U.S. Patent and Trademark Office.
Aug. 4, 2003, U.S. Patent 6,699,885 (U.S. Appl. No. 10/054,350)—Information Disclosure Statement Filed with the U.S. Patent and Trademark Office.
Jul. 25, 2003, U.S. Patent 6,780,882 (U.S. Appl. No. 10/260,132)—Information Disclosure Statement Filed with the U.S. Patent and Trademark Office.
Aug. 4, 2003, U.S. Patent 6,780,882 (U.S. Appl. No. 10/261,132)—Information Disclosure Statement Filed with the U.S. Patent and Trademark Office.
Jul. 23, 2003, U.S. Publication 20033215527 (U.S. Appl. No. 10/407,552)—Information Disclosure Statement Filed with the U.S. Patent and Trademark Office.
Aug. 4, 2003, U.S. Publication 20033215527 (U.S. Appl. No. 10/407,552)—Information Disclosure Statement Filed with the U.S. Patent and Trademark Office.
Feb. 16, 2005, U.S. Publication 20033215527 (U.S. Appl. No. 10/407,552)—Information Disclosure Statement Filed with the U.S. Patent and Trademark Office.
Mar. 4, 2005, U.S. Publication 20033215527 (U.S. Appl. No. 10/407,552)—Information Disclosure Statement Filed with the U.S. Patent and Trademark Office.
May 11, 2005, U.S. Publication 20033215527 (U.S. Appl. No. 10/407,552)—Information Disclosure Statement Filed with the U.S. Patent and Trademark Office.
Sep. 29, 2005, U.S. Publication 20033215527 (U.S. Appl. No. 10/407,552)—Information Disclosure Statement Filed with the U.S. Patent and Trademark Office.
Nov. 8, 2005, U.S. Publication 20033215527 (U.S. Appl. No. 10/407,552)—Information Disclosure Statement Filed with the U.S. Patent and Trademark Office.
Nov. 30, 2006, U.S. Publication 20033215527 (U.S. Appl. No. 10/407,552)—Information Disclosure Statement Filed with the U.S. Patent and Trademark Office.
Nov. 12, 2007, U.S. Publication 20033215527 (U.S. Appl. No. 10/407,552)—Information Disclosure Statement Filed with the U.S. Patent and Trademark Office.
Apr. 17, 2008, U.S. Publication 20033215527 (U.S. Appl. No. 10/407,552)—Information Disclosure Statement Filed with the U.S. Patent and Trademark Office.
May 21, 2008, U.S. Publication 20033215527 (U.S. Appl. No. 10/407,552)—Information Disclosure Statement Filed with the U.S. Patent and Trademark Office.
Jul. 25, 2003, U.S. Publication 20040048896 (U.S. Appl. No. 10/418,410)—Information Disclosure Statement Filed with the U.S. Patent and Trademark Office.
Aug. 4, 2003, U.S. Publication 20040048896 (U.S. Appl. No. 10/418,410)—Information Disclosure Statement Filed with the U.S. Patent and Trademark Office.
Dec. 16, 2004, U.S. Publication 20040048896 (U.S. Appl. No. 10/418,410)—Information Disclosure Statement Filed with the U.S. Patent and Trademark Office.
Mar. 4, 2005, U.S. Publication 20040048896 (U.S. Appl. No. 10/418,410)—Information Disclosure Statement Filed with the U.S. Patent and Trademark Office.
Sep. 20, 2005, U.S. Publication 20040048896 (U.S. Appl. No. 10/418,410)—Information Disclosure Statement Filed with the U.S. Patent and Trademark Office.
Apr. 14, 2006, U.S. Publication 20040048896 (U.S. Appl. No. 10/418,410)—Information Disclosure Statement Filed with the U.S. Patent and Trademark Office.
Nov. 12, 2007, U.S. Publication 20040048896 (U.S. Appl. No. 10/418,410)—Information Disclosure Statement Filed with the U.S. Patent and Trademark Office.
Apr. 17, 2008, U.S. Publication 20040048896 (U.S. Appl. No. 10/418,410)—Information Disclosure Statement Filed with the U.S. Patent and Trademark Office.
May 21, 2008, U.S. Publication 20040048896 (U.S. Appl. No. 10/418,410)—Information Disclosure Statement Filed with the U.S. Patent and Trademark Office.
Dec. 16, 2004, U.S. Publication 20040058018 (U.S. Appl. No. 10/641,732)—Information Disclosure Statement Filed with the U.S. Patent and Trademark Office.
Mar. 4, 2005, U.S. Publication 20040058018 (U.S. Appl. No. 10/641,732)—Information Disclosure Statement Filed with the U.S. Patent and Tradmark Office.
May 13, 2005, U.S. Publication 20040058018 (U.S. Appl. No. 10/641,732)—Information Disclosure Statement Filed with the U.S. Patent and Trademark Office.
Sep. 29, 2005, U.S. Publication 20040058018 (U.S. Appl. No. 10/641,732)—Information Disclosure Statement Filed with the U.S. Patent and Trademark Office.
Nov. 8, 2005, U.S. Publication 20040058018 (U.S. Appl. No. 10/641,732)—Information Disclosure Statement Filed with the U.S. Patent and Trademark Office.
Oct. 10, 2007, U.S. Publication 20040058018 (U.S. Appl. No. 10/641,732)—Information Disclosure Statement Filed with the U.S. Patent and Trademark Office.
Nov. 12, 2007, U.S. Publication 20040058018 (U.S. Appl. No. 10/641,732)—Information Disclosure Statement Filed with the U.S. Patent and Trademark Office.
Jan. 24, 2008, U.S. Publication 20040058018 (U.S. Appl. No. 10/641,732)—Information Disclosure Statement Filed with the U.S. Patent and Trademark Office.
Apr. 16, 2008, U.S. Publication 20040058018 (U.S. Appl. No. 10/641,732)—Information Disclosure Statement Filed with the U.S. Patent and Trademark Office.
May 2, 2008, U.S. Publication 20040058018 (U.S. Appl. No. 10/641,732)—Information Disclosure Statement Filed with the U.S. Patent and Trademark Office.
Dec. 16, 2004, U.S. Publication 20040171646 (U.S. Appl. No. 10/722,184)—Information Disclosure Statement Filed with the U.S. Patent and Trademark Office.
Mar. 4, 2005, U.S. Publication 20040171646 (U.S. Appl. No. 10/722,184)—Information Disclosure Statement Filed with the U.S. Patent and Trademark Office.
Sep. 9, 2005, U.S. Publication 20040171646 (U.S. Appl. No. 10/722,184)—Information Disclosure Statement Filed with the U.S. Patent and Trademark Office.
May 25, 2006, U.S. Publication 20040171646 (U.S. Appl. No. 10/722,184)—Information Disclosure Statement Filed with the U.S. Patent and Trademark Office.
Oct. 31, 2007, U.S. Publication 20040171646 (U.S. Appl. No. 10/722,184)—Information Disclosure Statement Filed with the U.S. Patent and Trademark Office.
Nov. 12, 2007, U.S. Publication 20040171646 (U.S. Appl. No. 10/722,184)—Information Disclosure Statement Filed with the U.S. Patent and Trademark Office.
Apr. 17, 2008, U.S. Publication 20040171646 (U.S. Appl. No. 10/722,184)—Information Disclosure Statement Filed with the U.S. Patent and Trademark Office.
May 21, 2008, U.S. Publication 20040171646 (U.S. Appl. No. 10/722,184)—Information Disclosure Statement Filed with the U.S. Patent and Trademark Office.
Mar. 7, 2005, U.S. Publication 20050042304 (U.S. Appl. No. 10/795,860)—Information Disclosure Statement Filed with the U.S. Patent and Trademark Office.

(56) References Cited

OTHER PUBLICATIONS

Sep. 20, 2005, U.S. Publication 20050042304 (U.S. Appl. No. 10/795,860)—Information Disclosure Statement Filed with the U.S. Patent and Trademark Office.
May 30, 2006, U.S. Publication 20050042304 (U.S. Appl. No. 10/795,860)—Information Disclosure Statement Filed with the U.S. Patent and Trademark Office.
Nov. 12, 2007, U.S. Publication 20050042304 (U.S. Appl. No. 10/795,860)—Information Disclosure Statement Filed with the U.S. Patent and Trademark Office.
Apr. 17, 2008, U.S. Publication 20050042304 (U.S. Appl. No. 10/795,860)—Information Disclosure Statement Filed with the U.S. Patent and Trademark Office.
May 21, 2008, U.S. Publication 20050042304 (U.S. Appl. No. 10/795,860)—Information Disclosure Statement Filed with the U.S. Patent and Trademark Office.
Mar. 7, 2005, U.S. Publication 20050004171 (U.S. Appl. No. 10/797,374)—Information Disclosure Statement Filed with the U.S. Patent and Trademark Office.
Sep. 9, 2005, U.S. Publication 20050004171 (U.S. Appl. No. 10/797,374)—Information Disclosure Statement Filed with the U.S. Patent and Trademark Office.
May 30, 2006, U.S. Publication 20050004171 (U.S. Appl. No. 10/797,374)—Information Disclosure Statement Filed with the U.S. Patent and Trademark Office.
Oct. 31, 2007, U.S. Publication 20050004171 (U.S. Appl. No. 10/797,374)—Information Disclosure Statement Filed with the U.S. Patent and Trademark Office.
Nov. 12, 2007, U.S. Publication 20050004171 (U.S. Appl. No. 10/797,374)—Information Disclosure Statement Filed with the U.S. Patent and Trademark Office.
Apr. 17, 2008, U.S. Publication 20050004171 (U.S. Appl. No. 10/797,374)—Information Disclosure Statement Filed with the U.S. Patent and Trademark Office.
May 21, 2008, U.S. Publication 20050004171 (U.S. Appl. No. 10/797,374)—Information Disclosure Statement Filed with the U.S. Patent and Trademark Office.
Mar. 7, 2005, U.S. Publication 20050054682 (U.S. Appl. No. 10/898,135)—Information Disclosure Statement Filed with the U.S. Patent and T rademark Office.
Sep. 9, 2005, U.S. Publication 20050054682 (U.S. Appl. No. 10/898,135)—Information Disclosure Statement Filed with the U.S. Patent and Trademark Office.
May 25, 2006, U.S. Publication 20050054682 (U.S. Appl. No. 10/898,135)—Information Disclosure Statement Filed with the U.S. Patent and Trademark Office.
Nov. 13, 2007, U.S. Publication 20050054682 (U.S. Appl. No. 10/898,135)—Information Disclosure Statement Filed with the U.S. Patent and Trademark Office.
Apr. 17, 2008, U.S. Publication 20050054682 (U.S. Appl. No. 10/898,135)—Information Disclosure Statement Filed with the U.S. Patent and Trademark Office.
May 21, 2008, U.S. Publication 20050054682 (U.S. Appl. No. 10/898,135)—Information Disclosure Statement Filed with the U.S. Patent and Trademark Office.
Aug. 22, 2005, Request for Ex Parte Reexamination Transmittal Form; Request for Reexamination Under 35 USC Sections 302-307 and 37 CFR Section 1.510 of U.S. Patent No. 6,699,885 Filed with the U.S. Patent Office, including Exhibits A-C. Additionally, Sep. 18, 2007, Ex Parte Reexamination Certificate for U.S. Patent No. 6,699,885.
File History of U.S. Appl. No. 90/007,686: Ex Parte Reexamination of U.S. Patent No. 6,699,885: Aug. 22, 2005, Request for Reexamination Aug. 26, 2005, Notice of Assignmet of Reexamination Request. Aug. 26, 2005, Notice of Reexamination Request Filing Date. Sep. 16, 2005, Reexmination Litigation Search Oct. 6, 2005, Order Granting Request for Ex Parte Reexamination. Mar. 23, 2006, Reexmination Litigation Search. Mar. 24, 2006, Non-Final Office Action in Ex Parte Reexamination. May 24, 2006, Amendment and Repose to the Office Action Dated Mar. 24, 2006. Aug. 15, 2006, Ex Parte Reexamination Interview Summary. Sep. 13, 2006, Applicant Summary of Interview with Examiner. Sep. 19, 2006, Declaration of Jeffery O. Philips. Sep. 21, 2006, Notice of Defective Paper in Ex Parte Reexamination. Sep. 28, 2006, Notice of Informal or Nonresponsive Amendment. Oct. 20, 2006, Reponse to Notice of Defective Paper in Ex Parte Rexxamination. Jan. 8, 2007, Supplemental Amendment A. Jan. 10, 2007, Reexmination Litigation Search Mar. 12, 2007, Notice of Intent to Issue Ex Parte Reexamination Certificate.
Mar. 12, 2007, Notice of Intent to Issue Ex Parte Reexamination Certificate for U.S. Patent No. 6,699,885 and Statement of Reasons for Patentability and/or Confirmation.
Aug. 3, 2007 Detailed Statement of the Factual and Legal Bases from Par Pharmaceutical to Santarus Inc. and The Curators of the University of Missouri.
Sep. 13, 2007 Complaint for Patent Infringement, *Santarus, Inc. and The Curators of the University of Missouri* v. *Par Pharmaceutical, Inc.* with Exhibits A-C, Case No. 07-551-GMS (D. Del.).
Sep. 14, 2007, Report on the Filing or Determination of an Action Regarding a Patent or Trademark, Case No. 07-551-GMS (D. Del.).
Oct. 2, 2007, First Amended Complaint for Patent Infringement, *Santarus, Inc. and The Curators of the University of Missouri* v. *Par Pharmaceutical, Inc.* with Exhibits A-D, Case No. 07-551-GMS (D. Del.).
Oct. 18, 2007, Answer and Counterclaim Filed by Par Pharmaceutical, Case No. 07-551-GMS (D. Del.).
Nov. 9, 2007, Reply to Counterclaims Filed by Santarus Inc. and The Curators of the University of Missouri, Case No. 07-551-GMS (D. Del.).
Nov. 13, 2007 Detailed Statement of the Factual and Legal Bases from Par Pharmaceutical to Santarus, Inc. and The Curators of the University of Missouri.
Dec. 6, 2007 Detailed Statement of the Factual and Legal Bases from Par Pharmaceutical to Santarus, Inc. and The Curators of the University of Missouri.
Dec. 20, 2007 Complaint for Patent Infringement, *Santarus, Inc. and The Curators of the University of Missouri* v. *Par Pharmaceutical* with Exs. A-E, Case No. 07-827 (D. Del.).
Dec. 20, 2007 Report of the Filing or Determination of an Action Regarding a Patent or Trademark, Case No. 07-827-GMS (D. Del.).
Jan. 10, 2008 Answer Filed by Par Pharmaceutical, Case No. 07-827-GMS (D. Del.).
Jan. 30, 2008 Amended Answer and Counterclaims filed by Par Pharmaceutical, Case No. 07-827-GMS (D. Del.).
Feb. 22, 2008 Plaintiff's Motion to Dismiss filed by Santarus, Inc., Case No. 07-551-GMS (D. Del.).
Feb. 22, 2008 Declaration of Joseph A. Mahoney in Support of Plaintiff's Motion to Dismiss filed by Santarus, Inc., Case No. 07-551-GMS (D. Del.).
Feb. 22, 2008 Reply to Counterclaims filed by Santarus, Inc., Case Nos. 07-827-GMS, 07-551-GMS (D. Del.).
Mar. 7, 2008 Defendant Par Pharmaceutical, Inc.'s Answering Brief in Opposition to Santarus' Motion to Dismiss, Case No. 07-551-GMS (D. Del.).
Mar. 17, 2008 Plaintiff Santarus, Inc.'s Reply Brief in Support of Its Motion to Dismiss, Case No. 07-551-GMS (D. Del.).
Mar. 19, 2008 The Curators of the University of Missouri's Rule 26(a)(1) Initial Disclosures, Case No. 07-551-GMS (D. Del.).
Mar. 19, 2008 Santarus Inc.'s Rule 26 Disclosures, Case No. 07-551-GMS (D. Del.).
Mar. 20, 2008 Defendant's Initial Disclosures Under Rule 26(a)(1)(A), Case No. 07-827-LPS and 07-551-LPS (D. Del.).
Jun. 11, 2008 Defendants' Response to Santarus's First Set of Interrogatories (Nos. 1-18), Case No. 07-551 (D. Del.).
Judgment and Opinion, *Santarus, Inc. and the Curators of the Univ. of Missouri* v. *Par Pharmaceutical, Inc.*, Case No. 2010-1360-1380 (Court of Appeals for the Federal Circuit, Dec. 17, 2012).
Judgment, *Santarus, Inc. and the Curators of the Univ. of Missouri* v. *Par Pharmaceutical, Inc.*, Case No. 07-551-GMS (D. Del. Apr. 21, 2010).
Memorandum (Decision by Judge Sleet), *Santarus, Inc. and the Curators of the Univ. of Missouri* v. *Par Pharmaceutical, Inc.*, Case No. 07-551-GMS (D. Del. Apr. 14, 2010).

(56) References Cited

OTHER PUBLICATIONS

Par's Findings of Fact and Conclusions of Law (Redacted), *Santarus, Inc. and the Curators of the Univ. of Missouri*v. *Par Pharmaceutical, Inc.*, Case No. 07-551-Gms (D. Del. Aug. 14, 2009).
Santarus and Univ. of Missouri's Proposed Findings of Fact and Conclusions of Law, *Santarus, Inc. and the Curators of the Univ. of Missouri* v. *Par Pharmaceutical, Inc.*, Case No. 07-551-GMS (D. Del. Aug. 14, 2009).
Trial Transcript, vol. A, *Santarus, Inc. and the Curators of the Univ. of Missouri*v. *Par Pharmaceutical, Inc.*, Case No. 07-551-GMS (D. Del. Jul., 13, 2009).
Trial Transcript, vol. B, *Santarus, Inc. and the Curators of the Univ. of Missouri*v. *Par Pharmaceutical, Inc.*, Case No. 07-551-GMS (D. Del. Jul. 14, 2009).
Trial Transcript, vol. C, *Santarus, Inc. and the Curators of the Univ. of Missouri*v. *Par Pharmaceutical, Inc.*, Case No. 07-551-GMS (D. Del. Jul. 15, 2009).
Trial Transcript, vol. D, *Santarus, Inc. and the Curators of the Univ. of Missouri* v. *Par Pharmaceutical, Inc.*, Case No. 07-551-GMS (D. Del. Jul. 16, 2009).
Trial Transcript, vol. E, *Santarus, Inc. and the Curators of the Univ. of Missouri*v. *Par Pharmaceutical, Inc.*, Case No. 07-551-GMS (D. Del. Jul. 17, 2009).
Letter from Par's counsel re: list of prior art, *Santarus, Inc. and the Curators of the Univ. of Missouri*v. *Par Pharmaceutical, Inc.*, Case No. 07-551-GMS (D. Del. Jun. 18, 2009).
Letter from Par's counsel re: narrowed list of prior art under 35 USC 282, *Santarus, Inc. and the Curators of the Univ. of Missouri* v. *Par Pharmaceutical, Inc.*, Case No. 07-551-GMS (D. Del. Jun. 29, 2009).
Joint Final Pretrial Order, *Santarus, Inc. and the Curators of the Univ. of Missouri* v. *Par Pharmaceutical, Inc.*, Case No. 07-551-GMS (D. Del. May 29, 2009).
J. Sleet's Amendment to Claims Construction Order of Nov. 5, 2008, *Santarus, Inc. and the Curators of the Univ. of Missouri* v. *Par Pharmaceutical, Inc.*, Case No. 07-551-GMS (D. Del. Dec. 17, 2008).
J. Sleet's Order Construing Claims of U.S. Patent Nos. 6,489,346; 6,669,885; and 6,645,988, *Santarus, Inc. and the Curators of the Univ. of Missouri* v. *Par Pharmaceutical, Inc.*, Case No. 07-551-GMS (D. Del. Nov. 5, 2008).
Skillman, et al., "The Gastric Mucosal Barrier: Clinical and Experimental Studies in Critically III and Normal Man, and in the Rabbit", Annals of Surgery, vol. 172, No. 4, pp. 564-584 (Oct. 1970).
Smythe, et al., "Changing Perspectives of Stress Gastritis Prophylaxis", The Annals of Pharmacotherapy, vol. 28, pp. 1073-1085 (Sep. 1994).
Spencer, et al., "Esomeprazole", Drugs, vol. 60, No. 2, pp. 321-329 (Aug. 2000).
Spychal, et al., "Thrombocytopenia Associated with Ranitidine", British Medical Journal, vol. 291, p. 1687 (Dec. 14, 1985).
Stratford, et al., "Nicotinamide Pharmacokinetics in Humans: Effect of Gastric Acid Inhibition, Comparison of Rectal vs. Oral Administration and the Use of Saliva for Drug Monitoring", British Journal of Cancer, vol. 74, No. 1, pp. 16-21 (Jul. 1996).
Tabata, et al., "Stabilization of a New Antiulcer Drug (Lansoprazole) in the Solid Dosage Forms", Drug Development and Industrial Pharmacy, vol. 18, No. 13, pp. 1437-1447 (1992).
Takeuchi, et al., "Effects of Pantoprazole, a Novel $H^+/K^+$-ATPase Inhibitor, on Duodenal Ulcerogenic and Healing Responses in Rats: A Comparative Study with Omeprazole and Lansoprazole", Journal of Gastroenterology and Hepatology, vol. 14, pp. 251-257 (1999).
Tanaka, et al., "Pathogenesis of the Earliest Epithelial Cell Damage Induced by Mepirizole and Cysteamine in the Rat Duodenum", Japanese Journal of Pharmacology, vol. 51, pp. 509-519 (1989).
Tanaka, et al., "Differential Stereoselective Pharmacokinetics of Pantoprazole, a Proton Pump Inhibitor in Extensive and Poor Metabolizers of Pantoprazole—A Preliminary Study", Chirality, vol. 9, pp. 17-21 (1997).
Thomson, "Are the Orally Administered Proton Pump Inhibitors Equivalent? A Comparison of Lansoprazole, Omeprazole, Pantoprazole and Rabeprazole", Current Gastroenterolgy Reports, vol. 2, pp. 482-493 (2000).
Tonini, et al., "Clinical Pharmacology and Safety Profile of Esomeprazole, the First Enantiomerically Pure Proton Pump Inhibitor", Digest Liver Dis., vol. 33, pp. 600-606 (2001).
Turns® Effecal Antacid: Instructions for Use on Bottle Labeling—Manufactured by SmithKline Beecham.
Trilateral Project B3b—Comparative Study on "reach-through claims".
Tryba, "Stress Ulcer Prophylaxis—Quo Vadis?", Intensive Care Medicine, vol. 20, pp. 311-313 (1994).
Amended Complaint, *Santarus, et al* v. *Dr. Reddy, D. NJ* —Case No. 12-CV-5202.
Answer and Counterclaims Amended Complaint, *Santarus, et al* v. *Dr. Reddy, D. NJ* —Case No. 12-CV-5202.
Defendants Opening Claim Construction Brief, *Santarus, et al* v. *Dr. Reddy, D. NJ* —Case No. 12-CV-5202, filed on May 17, 2013.
Defendants Opening Claim Construction Brief, *Santarus, et al* v. *Dr. Reddy, D. NJ* —Case No. 12-CV-5202, filed on May 20, 2013.
Plaintiffs Opening Markman Brief, *Santarus, et al* v. *Dr. Reddy, D. NJ* —Case No. 12-CV-5202.
Complaint, *Schering-Plough, et al* v. *Perrigo, D. NJ* —Case No. 10-CV-4838.
Amended Complaint, *MSD Consumer Products* v. *Par, D. NJ* —Case No. 10-CV-4837.
Answer to Amended Complaint, *MSD Consumer Products* v. *Par, D. NJ* —Case No. 10-CV-4837.
Par's Opening Claim Construction Brief, *MSD Consumer Products* v. *Par, D. NJ* —Case No. 10-CV-4837.
Par's Responsive Claim Construction Brief, *MSD Consumer Products* v. *Par, D. NJ* —Case No. 10-CV-4837.
Plaintiffs Response Markman Brief, *MSD Consumer Products* v. *Par, D. NJ* —Case No. 10-CV-4837.
Amended Complaint, *MSD Consumer Products* v. *Zydus, D. NJ* —Case No. 11-CV-7437.
Amended Complaint, *Santarus, et al* v. *Zydus, D. NJ* —Case No. 11-CV-7441.
Answer to Amended Complaint, *MSD Consumer Products* v. *Zydus, D. NJ* —Case No. 11-CV-7437.
Answer to Amended Complaint, *Santarus, et al* v. *Zydus, D. NJ* —Case No. 11-CV-7441.
Civil Docket, *Santarus Inc. et al* v. *Par Pharmaceutical Inc.*; Case #: 1:07-cv-00551-GMS (D. Del.) Downloaded on Apr. 28, 2014; 39 pages.
Civil Docket, *Schering-Plough Healthcare Products, Inc. et al* v. *Par Pharmaceutical, Inc.*; Case #: 3:10-cv-04837-PGS-LHG (D. NJ) Downloaded on Apr. 28, 2014; 17 pages.
Civil Docket, *Schering-Plough Healthcare Products, Inc. et al* v. *Perrigo Company et al*; Case #: 3:10-cv-04838-FLW-LHG (D. NJ) Downloaded on Apr. 28, 2014; 3 pages.
Civil Docket, *MSD Consumer Products, Inc. et al* v. *Zydus Pharmaceuticals (USA) Inc.*; Case #: 3:11-cv-07437-PGS-LHG (D. NJ) Downloaded on Apr. 28, 2014; 3 pages.
Civil Docket, *Santarus, Inc. et al* v. *Zydus Pharmaceuticals (USA) Inc.*; Case #: 3:11-cv-07441-PGS-LHG (D. NJ) Downloaded on Apr. 28, 2014; 19 pages.
Civil Docket, *Santarus, Inc. et al* v. *Dr. Reddy's Laboratories Inc. et al*; Case #: 3:12-cv-05202-PGS-LHG (D. NJ) Downloaded on Apr. 28, 2014; 8 pages.
Journal of Clinical Therapeutics & Medicines Nakagawa et al. vol. 7, No. 1, pp. 33-50 Abstract is inclosed, 1991.
Wade, Organic Chemistry, p. 349, Pritice-Hall, Inc. 1987.
*The American Midical Association Drug Evaluation,* vol. II, Gastrointestinal Drugs; Bennett, DR, Dickson BD (eds.) The American Medical Association, Chicago 1:8.
Andersson et al., (1993) Pharmacokinetics of [14C] omeprazole in patients with liver cirrhosis. *Clin. Pharmacokinet.,* 24(1): 71-8.
Andersson et al., (1990) Pharmacokinetics and bioavailability of omerprazole after single and repeated oral administration . . . *Br. J. Clin. Pharmacol.,* 29(5):557-63.

(56) References Cited

OTHER PUBLICATIONS

Andersson et al., (1990) Pharmacokinetics of various single intravenous and oral doses of omeprazole. *Eur. J. Clin. Pharmacol.,* 39(2):195-7.
Ballesteros et al., (1990) Bolus or intravenous infusion of ranitidine: effects on gastric pH and acid secretion . . . *Ann. Intern. Med.,* 112:334-339.
Barie and Hariri (1992) Therapeutic use of omeprazole for refractory stress-induced gastric mucosal hemorrhage. *Crit. Care Med.,* 20:899-901.
Bone (1991) Let's agree on terminology: definition of sepsis. *Crit. Care Med.,* 19:27.
Borreo et al., (1986) Antacids vs sucralfate in preventing acute gastrointestinal tract bleeding in abdominal aortic surgery. *Arch. Surg.,* 121:810-812.
Brunton (1990) in *The Pharmacologic Basis of Therapeutics.* Goodman AG, Rall TW, Nies AS, Taylor P (eds), New York, p. 907.
Cantu and Korek (1991) Central nervous system reactions to histamine-2 receptor blockers. *Ann Intern Med,* 114:1027-1034.
Cioffi et al., (1994) Comparison of acid neutralizing and non-acid neutralizing stress ulcer prophylaxis in thermally injured patients. *J. Trauma,* 36:541-547.
Cook et al., (1994) Risk factors for gastrointestinal bleeding in critically ill patients. *N. Engl. J. Med.,* 330:377-381.
Cook et al., (1991) Stress ulcer prophylaxis in the critically ill: a meta-analysis. *Am. J. Med.,* 91:519-527.
Cook et al., (1991) Nasocomial pneumonia and the role of gastric pH: a meta-analysis. *Chest,* 100:7-13.
Czaja et al., (1974) Acute gastroduodenal disease after thermal injury: an endoscopic evaluation of incidence and natural history. *N. Engl. J. Med.,* 291:925-929.
Dobkin et al., (1990) Does pH paper accurately reflect gastric ph? *Crit. Care Med.,* 18:985-988.
Driks et al., (1987) Nosocomial pneumonia in intubated patients given sucralfate as compared with antacids or histamine type 2 blockers. *N. Engl. J. Med.,* 317:1376-1382.
Eisenberg et al., (1990) Prospective trial comparing a combination pH probe-nasogastric tube with aspirated gastric pH . . . *Crit. Care Med.,* 18:1092-1095.
Fabian et al., (1993) Pneumonia and stress ulceration in severly injured patients. *Arch. Surg.,* 128:1855.
Fellenius et al. (1981) Substituted benzimidazoles inhibit gastric acid secretion by blocking H+/K+-ATPAse. *Nature,* 290:159-161.
Fiddian-Green et al., (1983) Predictive value of intramural pH and other risk factos for massive bleeding from stress ulceration. *Gastroenterology,* 8:613-620.
Fryklund et al. (1988) Function and structure of parietal cells after H+/K+-ATPase blockade. *Am. J. Physiol,* 254 (3 pt 1); G399-407.
Gafter et al., (1989) Thrombocytopenia associated with hypersensitivity to rantidine: possible cross-reactivity . . . *Am. J. Gastroenterol.,* 64:560-562.
Garner et al., (1988) CDC definitions for nosocomial infections. *Am. J. Infect. Control.,* 16:128-140.
Heath et al., (1988) Intragastic pH measurement using a novel disposable sensor. *Intens. Care Med.,* 14:232-235.
Kiilerich et al., (1995) Effect of intravenous infusion of omeprazole and ranitidine on twenty-four-hour intragastic pH . . . *Digestion,* 56:25-30.
Laggner et al., (1989) Prevention of upper gastrointestinal bleeding in long-term ventilated patients. *Am. J. Med.,* 86(suppl 6A):81-84.
Landahl et al., (1992) Pharmacokinetic study of omeprazole in elderly healthy volunteers. *Clin. Pharmacokinet.,* Dec:23(6):469-76.
Larson et al., (1984) Gastric response to severe head injury. *Am. J. Surg.,* 147:97-105.
Marrone and Silen, (1984) Pathogenesis, diagnosis and treatment of acute gastric mucosa lesions. *Clin. Gastroenterol,* 13:635-650.
Martin et al., (1993) Continuous intravenous cimetidine decreases stress-related upper gastrointestinal hemorrhage . . . *Crit. Care Med.,* 21:19-39.
Martin et al., (1992) Stress ulcers and organ failure in intubated patients in surgical intensive care units. *Ann. Surg.,* 215:332-337.
Meiners et al., (1982) Evaluation of various techniques to monitor intragastic pH. *Arch. Surg.,* 117:288-291.
Oh and Carroll (1994) Electrolyte and acid-base disorders. in *The Pharmacologic Approach to the Critically Ill Patient.* (Chernow B, ed) Williams & Wilkins, Baltimore, pp. 966-967.
Ostro et al. (1985) Control of gastric pH with cimetidine boluses versus primed infusions. *Gastroeneterology,* 89:532-537.
Peura and Johnson (1985) Cimetidine for prevention and treatment of gastroduodenal mucosal lesions in patients . . . *Ann Intern Med.,* 103:173-177.
Phillips and Metzler (1994) Simplified omeprazole solution for the prophylaxis of stress-related mucosal damage . . . *Crit. Care Med.,* 22:A53.
Pickworth et al., (1993) Occurrence of nasocomial pneumonia in mechanically ventilated trauma patients . . . *Crit. Care Med.,* 12:1856-1862.
Pilbrant et al. (1985) Development of an oral formulation of omeprazole. *Gastroenterol Suppl.,* 108:113-20.
Priebe and Skillman, (1981) Methods of prophylaxis in stress ulcer disease. *World J. Surg.,* 5:223-233.
Regardh et al., (1990) The pharmacokinetics of omeprazole in humans—a study of single intravenous and oral doses. *Ther. Drug Monit.,* Mar: 12(2):163-72.
Ryan et al., (1993) Nasocomial pneumonia during stress ulcer prophylaxis with cimetidine and sucralfate. *Arch. Surg.,* 128:1353-1357.
Sax (1987) Clinically important adverse effects and drug interactions with H2-receptor antagonists: an update. *Pharmacotherapy,* 7(6 pt 2):110S-115S.
Schepp (1993) Stress ulcer prophylaxis: still a valid option in the 1990? *Digestion,* 54:189-199.
Schuman et al., (1987) Prophylactic therapy for acute ulcer bleeding: a reappraisal. *Ann Intern. Med.,* 106:562-567.
Schuster (1993) Stress ulcer prophylaxis: in whom? with what? *Crit. Care Med.,* 21:4-6.
Siepler (1986) A dosage alternative for H-2 receptor antagonists, continuous-infusion. *Clin. Ther.,* 8(Suppl A):24-33.
Simms et al., (1991) Role of gastric colonizmation in the development of pneumonia in critically ill trauma patients . . . *J. Trauma,* 31:531-536.
Skillman et al., (1969) Respiratory failure, hypotension, sepsis and jaundice: a clinical syndrome associated with lethal . . . *Am. J. Surg.,* 117:523-530.
Skillman et al., (1970) The gastric mucosal barrier: clinical and experimental studies in critically ill and normal man . . . *Ann Surg.,* 172:564-584.
Smythe and Zarowitz (1994) Changing perspectives of stress gastritis prophylaxis. *Ann Pharmacother.,* 28:1073-1084.
Spychal and Wickham (1985) Thrombocytopenia associated with ranitidine. *Br. Med. J.,* 291:1687.
Tryba (1994) Stress ulcer prophylaxis—quo vadis? *Intens. Care Med.,* 20:311-313.
Tryba (1987) Risk of acute stress bleeding and nosocmial pneumonia in ventilated intensive care patients. Sucralfate vs. antacids. *Am. J. Med.,* 87(3B):117-124.
Vial et al., (1991) Side effects of ranitidine. *Drug Saf.,* 6:94-117.
Wallmark et al., (1985) The relationship between gastric acid secretion and gastric H+/K+-ATPase activity. *J. Biol. Chem.,* 260:13681-13684.
Wilder-Smith and Merki (1992) Tolerance during dosing with H2 receptor antagonists. An overview. *Scand. J. Gastroenterol.,* 27(suppl 193):14-19.
Zinner et al., (1981) The prevention of gastro-intestinal tract bleeding in patients in an intensive care unit. *Surg. Gynecol. Obstet.,* 153:214-220.
Gray et al. (1985) Influence of insulin antibodies on pharmacokinetics and bioavailability of recombinant human . . . *British Medical Journal,* 290:1687-1690.
Lind et al., (1986) Inhibition of basal and betazole- and sham-feeding-induced acid secretion by omeprazole in man. *Scand. J. Gastroenterol,* 21:1004-1010.
Nakagawa et al., (1991) Lansoprazole: Phase I Study of Lansoprazole (AG-1749) antiulcer agent Abstract in english; text in Japanese.

* cited by examiner

OVERALL PATIENT ENROLLMENT SCHEME

OMEPRAZOLE SOLUTION AND METHOD FOR USING SAME

Matter enclosed in heavy brackets [ ] appears in the original patent but forms no part of this reissue specification; matter printed in italics indicates the additions made by reissue.

This application is a continuation-in-part of U.S. Prov. App. Ser. No. 60/009,608 filed on Jan. 4, 1996.

TECHNICAL FIELD

The present invention relates to a pharmaceutical preparation containing a substituted benzimidazole. More particularly, the present invention relates to a substituted benzimidazole solution/suspension suitable for oral administration.

BACKGROUND OF THE INVENTION

Omeprazole is a substituted benzimidazole, 5-methoxy-2-[(4-methoxy-3,5-dimethyl-2-pyridinyl) methyl] sulfinyl]-1H-benzimidazole, that inhibits gastric acid secretion. Omeprazole belongs to a class of antisecretory compounds, the substituted benzimidazoles, that do not exhibit anti-cholinergic or $H_2$ histamine antagonist properties. Drugs of this class suppress gastric acid secretion by the specific inhibition of the $H^+/K^+$ ATPase enzyme system at the secretory surface of the gastric parietal cell.

Typically, omeprazole in the form of a delayed-release capsule, is prescribed for short-term treatment of active duodenal ulcers, gastric ulcers, gastroesophageal reflux disease (GERD), severe erosive esophagitis, poorly responsive systematic GERD, and pathological hypersecretory conditions such as Zollinger Ellison syndrome. These conditions are caused by an imbalance between acid and pepsin production, called aggressive factors, and mucous, bicarbonate, and prostaglandin production, called defensive factors.

These above-listed conditions commonly arise in healthy or critically ill patients and may be accompanied by significant upper gastrointestinal bleeding. $H_2$ antagonists, antacids, and sucralfate are commonly administered to minimize the pain and the complications related to these conditions. These drugs have certain disadvantages associated with their use. Some of these drugs are not completely effective in the treatment of the aforementioned conditions and/or produce adverse side effects, such as mental confusion, constipation, diarrhea, thrombocytopenia, (lowered platelet count) and/or are relatively costly modes of therapy as they require the use of automated infusion pumps for continuous intravenous delivery.

Patients with significant physiologic stress are at risk for stress-related gastric mucosal damage and subsequent upper gastrointestinal bleeding (Marrone and Silen, 1984). Risk factors that have been clearly associated with the development of stress-related mucosal damage are mechanical ventilation, coagulopathy, extensive burns, head injury, and organ transplant (Zinner et al., 1981; Larson et al., 1984; Czaja et al., 1974; Skillman et al., 1969; and Cook et al., 1994). One or more of these factors are often found in critically ill, intensive care unit patients. A recent cohort study challenges other risk factors previously identified such as acid-base disorders, multiple trauma, significant hypertension, major surgery, multiple operative procedures, acute renal failure, sepsis, and coma (Cook et al., 1994). Regardless of the risk type, stress-related mucosal damage results in significant morbidity and mortality. Clinically significant bleeding occurs in at least twenty percent of patients with one or more risk factors who are left untreated (Martin et al., 1993). Of those who bleed, approximately ten percent require surgery (usually gastrectomy) with a reported mortality of thirty percent to fifty percent (Czaja et al., 1974; Peura and Johnson, 1985). Those who do not need surgery often require multiple transfusions and prolonged hospitalization. Prevention of stress-related upper gastrointestinal bleeding is an important clinical goal.

In addition to general supportive care, the use of drugs to prevent stress-related mucosal damage is considered by many to be the standard of care (AMA Drug Evaluations). However, general consensus is lacking about which drugs to use in this setting (Martin et al., 1993; Gafter et al., 1989; Martin et al., 1992). In two recent meta-analyses (Cook et al., 1991; Tryba, 1994), antacids, sucralfate, and $H_2$-antagonists were all found to be superior to placebo and similar to one another in preventing upper gastrointestinal bleeding. Yet, prophylactic agents are withdrawn in fifteen to twenty percent of patients in which they are employed because of failure to prevent bleeding, or control pH (Ostro et al., 1985; Siepler, 1986; Ballesteros et al., 1990), or because of adverse effects (Gafter et al., 1989; Sax, 1987; Vial et al., 1991; Cantu and Korek, 1991; Spychal and Wickham, 1985). In addition, the characteristics of an ideal agent for the prophylaxis of stress gastritis and concluded that none of the agents currently in use fulfill their criteria (Smythe and Zarowitz, 1994).

Omeprazole reduces gastric acid production by irreversibly inhibiting the H+/K+ ATPase of the parietal cell—the final common pathway for gastric acid secretion (Fellenius et al., 1981; Wallmark et al., 1985; Frylund et al., 1988). Because this drug maintains gastric pH control throughout the dosing interval and has a very good safety profile, it is a logical choice for stress ulcer prophylaxis. The absence of an intravenous or oral liquid dosage form in the United States, however, has limited the testing and use of omeprazole in the critical care patient population. Subsequently, Barie et al (Barie and Hariri, 1992) described the use of omeprazole enteric-coated pellets administered through a nasogastric tube to control gastrointestinal hemorrhage in a critical care patient with multi-organ failure.

Stress ulcer prophylaxis has become routine therapy in intensive care units in most hospitals (Fabian et al, 1993.; Cook et al., 1991). Controversy remains regarding pharmacologic intervention to prevent stress-related bleeding in critical care patients. It has been suggested that the incidence and risk of gastrointestinal bleeding has decreased in the last ten years and drug therapy may no longer be needed (Cook et al., 1994; Tryba, 1994; Schepp, 1993). This reasoning is not supported by a recent placebo-controlled study. Martin et al. conducted a prospective, randomized, double-blind, placebo-controlled comparison of continuous-infusion cimetidine and placebo for the prophylaxis of stress-related mucosal damage (Marten et al., 1993). The study was terminated early because of excessive bleeding-related mortality in the placebo group. It appears that the natural course of stress-related mucosal damage in a patient at risk who receives no prophylaxis remains significant. In the placebo group, thirty-three percent of patients developed clinically significant bleeding, nine percent required transfusion, and six percent died due to bleeding-related complications. In comparison, fourteen percent of cimetidine-treated patients developed clinically significant bleeding, six percent required transfusions, and 1.5% died due to bleeding-related complication; the difference in bleeding rates between treatment groups was statistically significant. This study clearly demonstrated that continuous-infusion cimetidine reduced morbidity in critical care patients. Although, these data were used to support the approval of continuous-infusion cimetidine by the Food and Drug Administration for stress ulcer prophylaxis, $H_2$-antagonists fall short of being the optimal pharmacotherapeutic agents for preventing of stress-related mucosal bleeding.

Another controversy surrounding stress ulcer prophylaxis is which drug to use. In addition to the various $H_2$-antagonists, antacids and sucralfate are other treatment options for the prophylaxis of stress-related mucosal damage. An ideal drug in this setting should possess the following characteristics: prevent stress ulcers and their complications, be devoid of toxicity, lack drug interactions, be selective, have minimal associated costs (such as personnel time and materials), and be easy to administer (Smythe and Zarowitz, 1994).

Some have suggested that sucralfate is possibly the ideal agent for stress ulcer prophylaxis (Smythe and Zarowitz, 1994). Randomized, controlled studies support the use of sucralfate (Borrero et al., 1986; Tryba, 1987; Cioffi et al., 1994; Driks et al., 1987), but data on critical care patients with head injury, trauma, or burns are limited. In addition, a recent study comparing sucralfate and cimetidine plus antacids for stress ulcer prophylaxis reported clinically significant bleeding in three of forty-eight (6%) sucralfate-treated patients, one of whom required a gastrectomy (Cioffi et al., 1994). In the study performed by Driks and coworkers that compared sucralfate to conventional therapy ($H_2$-antagonists, antacids, or $H_2$-antagonists plus antacids), the only patient whose death was attributed to stress-related upper gastrointestinal bleeding was in the sucralfate arm (Driks et al., 1987).

$H_2$-antagonists fulfill many of the criteria for an ideal stress ulcer prophylaxis drug. Yet, clinically significant bleeds can occur during $H_2$-antagonist prophylaxis (Martin et al., 1993; Cook et al., 1991; Schuman et al., 1987) and adverse events are not uncommon in the critical care population (Gafter et al., 1989; Sax, 1987, Vial et al., 1991; Cantu and Korek, 1991; Spychal and Wickham, 1985). One reason proposed for the therapeutic $H_2$-antagonist failures is lack of pH control throughout the treatment period (Ostro et al., 1985). Although the precise pathophysiologic mechanism(s) involved in stress ulceration are not clearly established, the high concentration of hydrogen ions in the mucosa (Fiddian-Green et al., 1987) or gastric fluid in contact with mucosal cells appears to be an important factor. A gastric pH >3.5 has been associated with a lower incidence of stress-related mucosal damage and bleeding (Larson et al., 1984; Skillman et al., 1969; Skillman et al., 1970; Priebe and Skillman, 1981). Several studies have shown that $H_2$-antagonists, even in maximal doses, do not reliably or continuously increase intragastric pH above commonly targeted levels (3.5 to 4.5). This is true especially when used in fixed-dose bolus regimens (Ostro, 1985; Siepler, 1986; Ballesteros et al., 1990). In addition, gastric pH levels tend to trend downward with time when using a continuous-infusion of $H_2$-antagonists, which may be the result of tachyphylaxis (Ostro et al., 1985; Wilder-Smith and Merki, 1992).

Because stress ulcer prophylaxis is frequently employed in the intensive care unit, it is essential from both a clinical and economic standpoint to optimize the pharmacotherapeutic approach. In an attempt to identify optimal therapy, cost of care becomes an issue. All treatment costs should be considered, including the costs of treatment failures and drug-related adverse events. While the actual number of failures resulting in mortality is low, morbidity (e.g., bleeding that requires blood transfusion) can be high, even though its association with the failure of a specific drug is often unrecognized.

Omeprazole represents an advantageous alternative to the use of $H_2$ antagonists, antacids, and sucralfate as a treatment for complications related to stress-related mucosal damage. However, in its current form (capsules containing an enteric-coated granule formulation of omeprazole), omeprazole can be difficult or impossible to administer to patients who are unable (critically ill patients, children, elderly, patients suffering from dysphagia) or patients who are either unwilling or unable to swallow tablets or capsules. Therefore, it would be desirable to formulate an omeprazole solution which can be enterally delivered to a patient thereby providing the benefits of omeprazole without the drawbacks of the current capsule dose form.

Omeprazole has been formulated in many different embodiments such as in a mixture of polyethylene glycols formed a mixture of adeps solidus and sodium lauryl sulfate in a soluble, basic amino acid to yield a formulation designed for administration in the rectum as shown in U.S. Pat. No. 5,219,870 to Kim. U.S. Pat No. 5,395,323 to Berglund ('323) discloses a device for mixing a pharmaceutical from a solid supply into a parenterally acceptable liquid form for parenteral administration to a patient. The '323 patent teaches the use of an omeprazole tablet which is placed in the device and dissolved by normal saline, and infused into the patient. This device and method of infusing omeprazole does not provide the omeprazole solution as an enteral product nor is this omeprazole solution directly administered to the diseased or affected areas, namely the stomach and upper gastrointestinal tract, nor does this omeprazole formulation provide the immediate anti-acid effect of the present formulation.

U.S. Pat. No. 4,786,505 to Lovgren et al., discloses a pharmaceutical preparation containing omeprazole together with an alkaline reacting compound or an alkaline salt of omeprazole optionally together with an alkaline compound as a core material in a tablet formulation. The use of the alkaline material, which can be chosen from such substances as the sodium salt of carbonic acid, are used to form a "micro-pH" around each omeprazole particle to protect the omeprazole which is highly sensitive to acid pH. The powder mixture is then formulated to small beads, pellets, tablets and may be loaded into capsules by conventional pharmaceutical procedures.

This formulation of omeprazole does not provide an omeprazole dose form which can be enterally administered to a patient who may be unable and/or unwilling to swallow capsules or pellets nor does it teach a convenient form which can be used to make an omeprazole solution.

Several buffered omeprazole solutions have been disclosed. Andersson et al., 1993; Landahl et al., 1992; Andersson et al., 1990; Regardh et al., 1990; Andersson et al., 1990; Pilbrant et al., 1985.

All of the buffered omeprazole solutions described in these references were administered orally and were given to healthy subjects who were able to ingest the oral dose. In all of these studies, omeprazole was suspended in a solution including sodium bicarbonate, as a pH buffer, in order to protect the acid sensitive omeprazole during administration.

In all of these studies, repeated administration of sodium bicarbonate both prior to, during, and following omeprazole administration were required in order to prevent acid degradation of the omeprazole given via the oral route of administration. As a result, the ingestion of the large amounts of sodium bicarbonate and large volumes of water were required. In the above-cited studies, as much as 48 mmoles of sodium bicarbonate in 300 ml of water must be ingested for a single dose of omeprazole to be orally administered.

Initial reports of increased frequency of pneumonia in patients receiving stress ulcer prophylaxis with agents that raise gastric pH has influenced the pharmacotherapeutic approach to management of critical care patients. However, several recent studies (Simms et al., 1991; Pickworth et al., 1993; Ryan et al., 1993; Fabian et al., 1993), a meta-analysis (Cook et al., 1991), and a closer examination of the studies that initiated the elevated pH-associated pneumonia hypotheses (Schepp, 1993) cast doubt on a causal relationship. The relationship between pneumonia and antacid therapy is much stronger than for $H_2$-antagonists. The shared effect of antacids and $H_2$-antagonists on gastric pH seems an irresistible common cause explanation for nosocomial pneumonia observed during stress ulcer prophylaxis. However, there are important differences between these agents that are not often emphasized (Laggner et al., 1989). When antacids are exclusively used to control pH in the prophylaxis of stress-related upper gastrointestinal bleeding, large volumes are needed. Volume, with or without subsequent reflux, may be the underlying mechanism(s) promoting the development of pneumonia in susceptible patient populations rather than the increased gastric pH. The rate of pneumonia in our study (12%) was not unexpected in this critical care population and compares with sucralfate, which does not significantly raise gastric pH (Pickworth et al., 1993; Ryan et al., 1993).

The buffered omeprazole solutions of the above cited prior art require large amounts of sodium bicarbonate to be given by repeated administration. This is necessary to prevent acid degradation of the omeprazole. The administration of large amounts of sodium bicarbonate can produce at least four significant adverse effects which can dramatically reduce the efficacy of the omeprazole in patients and reduce the overall health of the patients. In the above-cited studies, basically healthy volunteers rather than sick patients were given only one or two dosages of omeprazole utilizing pre-dosing and post-dosing with large volumes of sodium bicarbonate. This dosing protocol would not be suitable for sick or critically ill patients who must receive multiple doses of omeprazole.

Since bicarbonate is usually neutralized in the stomach or is absorbed, such that belching results, patients with gastroesophageal reflux may exacerbate or worsen their gastroesophageal reflux disease as the belching can cause upward movement of stomach acid (Brunton, 1990).

Patients with conditions, such as hypertension or heart failure, are standardly advised to avoid the intake of excessive sodium as this can cause aggravation or exacerbation of their hypertensive conditions (Brunton, 1990).

Additionally, patients with numerous conditions which typically accompany critical illness should avoid the intake of excessive sodium bicarbonate as it can cause metabolic alkalosis which can result in a serious worsening of the patient's condition. Furthermore, excessive antacid intake (such as sodium bicarbonate) can result in drug interactions which produce serious adverse effects. For example, by altering gastric and urinary pH, antacids can alter rates of drug dissolution and absorption, bioavailability, and renal elimination (Brunton, 1990).

Since buffered omeprazole solution requires prolonged administration of the antacid, sodium bicarbonate, it makes it difficult for patients to comply with the above recommendation.

In addition to the disadvantages associated with excessive intake of sodium bicarbonate, the above-cited prior art teaches a relatively complex regimen for the oral administration of omeprazole. For example, in the Pilbrant et al. (1985) reference, the oral omeprazole administration protocol calls for administering to a subject who has been fasting for at least ten hours, a solution of 8 mmoles of sodium bicarbonate in 50 ml of water. Five minutes later, the subject ingests a suspension of 60 mg of omeprazole in 50 ml of water which also contains 8 mmoles of sodium bicarbonate. This is rinsed down with another 50 ml of 8 mmoles sodium bicarbonate solution. Ten minutes after the ingestion of the omeprazole dose, the subject ingests 50 ml of bicarbonate solution (8 mmoles). This is repeated at twenty minutes and thirty minutes post omeprazole dosing to yield a total of 48 mmoles of sodium bicarbonate and 300 ml of water in total which are ingested by the subject for a single omeprazole dose.

Not only does this regimen require the ingestion of excessive amounts of bicarbonate and water, it is unlikely that a healthy patient would comply with this regimen for each dose of omeprazole over the course of a prescribed omeprazole protocol. It is unlikely or even improbable that a critically ill patient would be able to comply with this regimen.

Even in healthy patients, the complexity of the drug regimen leads to the conclusion that patients would be unlikely to comply with this regimen thereby leading to a lack of beneficial outcome for the patient. It is well documented that patients who are required to follow complex schedules for drug administration are non-compliant and, thus, the efficacy of the buffered omeprazole solutions of the prior art would be expected to be reduced due to non-compliance. Compliance has been found to be markedly reduced when patients are required to deviate from a schedule of one or two (usually morning and night) doses of a medication per day. The use of the prior art buffered omeprazole solutions which require administration protocols with numerous steps, different drugs (sodium bicarbonate+omeprazole+PEG400 versus sodium bicarbonate alone), and specific time allotments between each stage of the total omeprazole regimen in order to achieve efficacious results is clearly in contrast with both current drug compliance theories and human nature.

The prior art (Pilbrant et al., 1985) teaches that the buffered omeprazole suspension can be stored at refrigerator temperatures for a week and deep frozen for a year while still maintaining 99% of their initial potency. It would be desirable to have an omeprazole solution which could be stored at room temperature or in a refrigerator for periods of time which exceed those of the prior art while still maintaining 99% of the initial potency. Additionally, it would be advantageous to have a form of the omeprazole and bicarbonate which can be utilized to instantly make the omeprazole solution/suspension of the present invention which is supplied in a solid form which imparts the advantages of improved shelf-life at room temperature, lower cost to produce, less expensive shipping costs, and which is less expensive to store.

It would, therefore, be desirable to have an omeprazole formulation which provides a cost effective means for the treatment of the aforementioned conditions without the adverse effect profile of $H_2$ receptor antagonist, antacids, and sucralfate. Further, it would be desirable to have an omeprazole formulation which is convenient to prepare and administer to patients unable ingest capsules, which is rapidly absorbed, can be enterally delivered directly to the desired treatment region, which does not clog indwelling tubes, such as nasogastric tubes or other similar tubes, and which acts as an antacid immediately upon delivery. Furthermore, it would be desirable to have a pharmaceutical composition which is highly efficacious for the treatment of the aforementioned conditions.

The present invention provides a solution/suspension of omeprazole, lansoprazole or other suitable benzimidazoles which is suitable for enteral administration which includes all of the aforementioned advantages.

SUMMARY OF THE INVENTION AND ADVANTAGES

In accordance with the present invention, there is provided a pharmaceutical composition including an aqueous solution/suspension of omeprazole or other substituted benzimidazoles and derivatives thereof in a pharmaceutically acceptable carrier including a bicarbonate salt of a Group IA metal.

The present invention further provides a method for treating and/or preventing gastrointestinal conditions by administering to a patient a pharmaceutical composition including an aqueous solution/suspension of omeprazole and derivatives thereof in a pharmaceutically acceptable carrier comprising a bicarbonate salt of a Group IA metal wherein the administration step consists of a single dosage without requiring further administration of the bicarbonate salt of the Group IA metal.

The present invention further provides a pharmaceutical composition for use making a solution/suspension of omeprazole or other substituted benzimidazoles and derivatives thereof.

BRIEF DESCRIPTION OF THE DRAWINGS

Other advantages of the present invention will be readily appreciated as the same becomes better understood by reference to the following detailed description when considered in connection with the accompanying drawing wherein.

DETAILED DESCRIPTION OF THE INVENTION

Figure 1:
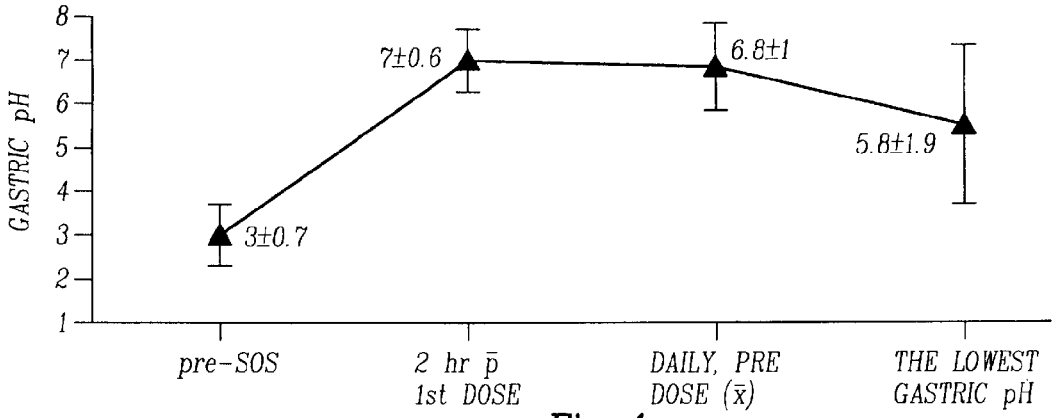
FIG. 1 is a graph showing the effect of the omeprazole solution/suspension of the present invention on gastric pH in patients at risk for upper gastrointestinal bleeding from stress-related mucosal damage.

A pharmaceutical composition which can include an aqueous solution/suspension of omeprazole or other substituted benzimidazoles such as lansoprazole, and derivatives thereof in a pharmaceutically acceptable carrier including a bicarbonate salt of a Group IA metal is disclosed. For the purposes of description, the composition includes both solutions and/or suspensions of the omeprazole or other substituted benzimidazoles. Hereinafter, the use of the term "solution" includes solutions and/or suspensions of the substituted benzimidazoles.

The pharmaceutical composition of the present invention is prepared by mixing omeprazole (Merck & Co. Inc., West Point, Pa.) or other substituted benzimidazoles and derivatives thereof with a solution including a bicarbonate salt of a Group IA metal. Preferably, omeprazole powder or granules, which can be obtained from a capsule, are mixed with a sodium bicarbonate solution to achieve a desired final omeprazole concentration. The concentration of omeprazole in the solution/suspension can range from approximately 0.5 mg/ml to approximately 6.0 mg/ml. The preferred concentration for the omeprazole in the solution/suspension ranges from approximately 1.0 mg/ml to approximately 4.0 mg/ml with 2 mg/ml being the standard concentration.

The pharmaceutically effective carrier includes the bicarbonate salt of the Group IA metal and can be prepared by mixing the bicarbonate salt of the Group IA metal, preferably sodium bicarbonate, with water. The concentration of the bicarbonate salt of the Group IA metal in the composition generally ranges from approximately 5.0 percent to approximately 60.0 percent. Preferably, the concentration of the bicarbonate salt of the Group IA metal ranges from approximately 7.5 percent to approximately 10.0 percent. In a preferred embodiment of the present invention, sodium bicarbonate is the preferred salt of the Group IA metal and is present in a concentration of approximately 8.4 percent.

In a preferred embodiment of the present invention, enterically-coated omeprazole particles are obtained from delayed release capsules (Astra Merck) additionally omeprazole powder can be used. The coated omeprazole particles are mixed with a sodium bicarbonate ($NaHCO_3$) solution which dissolves the enteric coating and forms an omeprazole solution/suspension in accordance with the present invention. It is important to emphasize that the enteric coated pellets of omeprazole must be allowed to completely breakdown in the suspension vehicle or carrier prior to administration. The omeprazole solution/suspension has significant pharmacokinetic advantages over standard time-release omeprazole capsules including: a decreased drug absorbance time (~10 to 12 minutes) following administration for the omeprazole solution versus (~2-3 hours) following administration for the enteric coated pellets; the $NaHCO_3$ solution protects the omeprazole from acid degradation prior to absorption; the $NaHCO_3$ acts as an antacid while the omeprazole is being absorbed; and the solution/suspension can be administered through an existing indwelling tube without clogging, for example, nasogastric or other feeding tubes (jejunal or duodenal) including small bore needle catheter feeding tubes.

As stated above, suitable derivatives of omeprazole can be substituted for the omeprazole or other suitable substituted benzimidazoles without departing from the spirit of the present invention. These derivatives can include, but are not limited to, lansoprozole.

The pharmaceutical composition including the omeprazole and derivatives thereof in a pharmaceutically acceptable carrier of a bicarbonate salt of Group IA metal can be used for the treatment of gastrointestinal conditions including, but not limited to, active duodenal ulcers, gastric ulcers, gastroesophageal reflux disease (GERD), severe erosive esophagitis, poorly responsive systematic GERD, and pathological hypersecretory conditions such as Zollinger Ellison Syndrome. These conditions are caused by imbalances between acid and pepsin production, called aggressive factors, and mucous, bicarbonate, and prostaglandin production, called defensive factors. Treatment of these conditions is accomplished by administering to a patient an effective amount of the pharmaceutical composition according to the present invention.

The omeprazole solution/suspension is administered and dosed in accordance with good medical practice, taking into account the clinical condition of the individual patient, the sight and method of administration, scheduling of administration, and other factors known to medical practitioners. The "effective amount" for purposes herein thus determine by such considerations as are known in the art. The amount must be effective to achieve improvement, including but not limited to, raising of gastric pH, reduced gastrointestinal bleeding, reduction in the need for blood transfusion, improved survival rate, more rapid recovery, or improvement or elimination of systems and other indicators as are selected as appropriate measures by those skilled in the art.

The dosage range of omeprazole or other substituted benzimidazoles and derivatives thereof can range from approximately 2 mg/day to approximately 100 mg/day. The standard daily dosage is typically 20 mg omeprazole in 10 ml of solution.

In the method of the present invention, the omeprazole solution/suspension can be administered in various ways. It should be noted that the omeprazole solution/suspension can be administered as the compound or as the pharmaceutically acceptable salt and can be administered alone or in combination with pharmaceutically acceptable carriers. The compounds can be administered orally or enterally. The formulations can be made more palatable by adding flavorings such as chocolate, root beer, and others.

Additionally, various additives including ambicin which enhance the stability, sterility, and isotonicity of the compositions. Additionally, antimicrobial preservatives, antioxidants, chelating agents, and buffers can be added. However, microbiological evidence shows that this formulation inherently possesses anti-microbial activity. Prevention of the action of microorganisms can be enhanced by various antibacterial and antifungal agents, for example, parabens, chlorobutanol, phenol, sorbic acid, and the like.

In many cases, it would be desirable to include isotonic agents, for example, sugars, sodium chloride, and the like. Additionally, thickening agents, such as methyl cellulose, in order to reduce settling the omeprazole or derivatives thereof from the suspension.

The formulations of the present invention can be manufactured in a concentrated form, such as an effervescent tablet, so that upon reaction with water, the aqueous form of the present invention would be produced for oral or enteral administration.

Additionally, the present invention can be manufactured by utilizing micronized omeprazole in place of the omeprazole granules or omeprazole powder in place of omeprazole granules. This process is known as micronization and is utilized in order to produce a particle having a greater diameter. Micronization is the process by which solid drug particles are reduced in size. Since the dissolution rate is directly proportional to the surface area of the solid, and reducing the particle size increases the surface area, reducing the particle size increases the dissolution rate.

Although micronization results in increased surface area causing particle aggregation, which can negate the benefit of micronization and is an expensive manufacturing step, it does have the significant benefit of increasing the dissolution rate of relatively water insoluble drugs, such as omeprazole.

A pharmacological formulation of the omeprazole solution/suspension utilized in the present invention can be administered orally to the patient. A pharmacological formulation of the omeprazole solution/suspension utilized in the present invention is preferably administered enterally. This can be accomplished, for example, by administering the solution/suspension via a nasogastric tube or other indwelling tubes. In order to avoid the critical disadvantages associated with administering large amounts of sodium bicarbonate, the omeprazole solution of the present invention is administered in a single dose which does not require any further administration of bicarbonate following the administration of the omeprazole solution. That is, unlike the prior art omeprazole solutions and administration protocols outlined above, the formulation of the present invention is given in a single dose which does not require administration of bicarbonate either before administration of the omeprazole or after administration of the omeprazole. The present invention eliminates the need to pre- or post-dose with additional volumes of water and sodium bicarbonate. The amount of bicarbonate administered via the single dose administration of the present invention is less than the amount of bicarbonate administered as taught in the prior art references cited above.

The amount of sodium bicarbonate used in the solution/suspension of the present invention is approximately 1 meq (or mmole) sodium bicarbonate per 2 mg omeprazole, with a range of approximately 0.75 meq (mmole) to 1.5 meq (mmole) per 2 mg of omeprazole.

The present invention further includes a pharmaceutical composition for making a solution/suspension of omeprazole or other substituted benzimidazoles and derivatives thereof, which consists essentially of omeprazole or other substituted benzimidazoles and derivatives thereof and a bicarbonate salt of a Group IA metal in a form convenient for storage, whereby when the composition is placed into a aqueous solution, the composition dissolves yielding a solution/suspension suitable for enteral administration to a subject. The pharmaceutical composition is in a solid form prior to dissolution in the aqueous solution. The omeprazole or other substituted benzimidazoles and derivatives thereof and bicarbonate can be formed into a tablet, capsules, or granules, by methods well known to those skilled in the art.

The pharmaceutical composition suitable for making a solution/suspension according to the present invention can further include an effervescing agent to aid in the dissolution of the pharmaceutical composition in the aqueous solution. In the present invention the effervescing agent is sodium bicarbonate.

The resultant omeprazole solution is stable at room temperature for several weeks and inhibits the growth of bacteria or fungi as shown in Example IV below. By providing a pharmaceutical composition including the omeprazole or other substituted benzimidazole and derivatives thereof with bicarbonate in a solid form, which is dissolved in a prescribed amount of aqueous solution to yield the desired concentration of omeprazole and bicarbonate, the cost of production, shipping, and storage are greatly reduced as no liquids are shipped (reducing weight and cost) and there is no need to refrigerate the solid form of the composition or the solution. The resultant solution, can be formulated and then used to provide dosages for a single patient over a course of time or for several patients.

The following experimental data illustrate the utility of the pharmaceutical composition of the present invention.

METHODS

EXAMPLE I

Patients were evaluable if they met the following criteria: had two or more risk factors for SRMD (mechanical ventilation, head injury, severe burn, sepsis, multiple trauma, adult respiratory distress syndrome, major surgery, acute renal failure, multiple operative procedures, coagulatherapy, significant hypotension, acid-base disorder, and hepatic failure), gastric pH of ≥4 prior to study entry, and no concomitant prophylaxis for SRMD.

Nasogastric (ng) tubes were placed in the patients and an omeprazole dosage protocol of 40 mg omeprazole solution/suspension followed by 40 mg omeprazole solution/suspension in eight hours, then 20 mg omeprazole solution/suspension per day, for five days. After each omeprazole solution/suspension administration, nasogastric suction was turned off for thirty minutes.

Results

Eleven patients were evaluable. All patients were mechanically ventilated. Two hours after the initial dose of omeprazole solution/suspension 40 mg omeprazole, all patients had an increase in gastric pH to greater than eight as shown in FIG. 1. Ten of the eleven patients maintained a gastric pH of greater than or equal to four on 20 mg omeprazole solution/suspension. One patient required 40 mg omeprazole solution/suspension per day (closed head injury, five total risk factors for SRMD). Two patients were changed to omeprazole solution/suspension after having developed clinically significant upper gastrointestinal bleeding while receiving conventional intravenous $H_2$ antagonists. Bleeding subsided in both cases after twenty-four hours. Clinically significant upper gastrointestinal bleeding did not occur in the other nine patients. Overall mortality was 27%, mortality attributable to upper gastrointestinal bleeding was 0%. Pneumonia developed in one patient after initiating omeprazole therapy and was present upon the initiation of omeprazole therapy in another patient. The mean length of prophylaxis was five days.

A pharmacoeconomic analysis revealed a difference in the total cost of care for the prophylaxis of SRMD:

ranitidine (Zantac®) continuous infusion intravenously (150 mg/24 hours)×five days $125.50;

cimetidine (Tagamet®) continuous infusion intravenously (900 mg/24 hours)×five days $109.61;

sucralfate one gm slurry four times a day per (ng) tube×five days $73.00; and

SOS regimen per (ng) tube×five days $65.70.

Conclusion

This example illustrates the efficacy of the simplified omeprazole solution of the present invention based on the increase in gastric pH, safety and cost/convenience of the omeprazole solution/suspension as a method for SRMD prophylaxis.

EXAMPLE II

Experiments were carried out in order to determine the effect of the omeprazole solution/suspension (omeprazole/sodium bicarbonate solution) administration on the accuracy on subsequent pH measurements through a nasogastric tube.

Methods

The omeprazole solution/suspension was prepared by mixing 10 ml of 8.4% sodium bicarbonate with the contents of a 20 mg capsule of omeprazole (Merck & Co. Inc., West Point, Pa.) to yield a solution/suspension having a final omeprazole concentration of 2 mg/ml. After mixing the omeprazole solution/suspension, it was administered into the stomach, usually, through a nasogastric (ng) tube. Nasogastric tubes from nine different institutions were gathered for an evaluation 400 mg omeprazole solution/suspension was prepared as described above. Artificial gastric fluid (gf) was prepared according to the USP. pH recordings were made in triplicate using a Microcomputer Portable pH meter model 6007 (Jeno Electronics Ltd., Taipai, Taiwan). [1] First the terminal portion (tp) of the nasogastric tubes was placed into a glass beaker containing the gastric fluid. A 5 ml aliquot of gastric fluid was aspirated through each tube and the pH recorded, this was called the "pre-omeprazole solution/suspension measurement". [2] Secondly, the terminal portion (tp) of each of the nasogastric tubes was removed from the beaker of gastric fluid and placed into an empty beaker. Twenty (20) mg of omeprazole solution/suspension was delivered through each of the nasogastric tubes and flushed with 10 ml of tap water. The terminal portion (tp) of each of the nasogastric tubes was placed back into the gastric fluid. After a one hour incubation, a 5 ml aliquot of gastric fluid was aspirated through each nasogastric tube and the pH recorded, this was called the "after 1st dose SOS measurement". [3] After an additional hour had passed, the second step was repeated, this was called the "after 2nd ND dose SOS measurement". In addition to the pre-SOS measurement, the pH of the gastric fluid was checked in triplicate after steps [2] and [3]. A change in the pH measurements of ±0.3 units was considered significant. The Friedman test was used to compare the results. The Friedman test is a two way analysis of variance which is used when more than two related samples are of interest, as in repeated measurements.

Results

The results of this experiments are outlined in Table 1. Table 1 illustrates the results of the pH measurements that were taken during the course of the experiment. These results illustrate that there were no statistically significantly latent effects of omeprazole solution/suspension administration (per nasogastric tube) on the accuracy of subsequent pH measurements obtained through the same nasogastric tube.

EXAMPLE III

Experiments were performed in order to determine the efficacy, safety, and cost of simplified omeprazole suspension in mechanically ventilated critically ill patients who have at least one additional risk factor for stress-related mucosal damage.

Methods

Patients

Seventy-five adult, mechanically ventilated patients with at least one additional risk factor for stress-related mucosal damage. Interventions: Patients received 20 ml omeprazole suspension (containing 40 mg of omeprazole) initially, followed by a second 20 ml dose six-eight hours later, then 10 ml (20 mg) daily. Omeprazole solution/suspension according to the present invention was administered through a nasogastric tube, followed by 5-10 ml of tap water. The nasogastric tube was clamped for one-two hours after each administration.

Measurements and Main Results

The primary outcome measure was clinically significant gastrointestinal bleeding determined by endoscopic evaluation, nasogastric aspirate examination, or heme-positive coffee ground material that did not clear with lavage and was associated with a five percent decrease in hematocrit. Secondary efficacy measures were gastric pH measured four hours after omeprazole was first administered, mean gastric pH after omeprazole was started, and the lowest gastric pH during omeprazole therapy. Safety-related outcomes included the incidence of adverse events and the incidence of pneumonia. No patient experienced clinically significant upper gastrointestinal bleeding after receiving omeprazole suspension. The four-hour post omeprazole gastric pH was 7.1 (mean), the mean gastric pH after starting omeprazole was 6.8 (mean) and the lowest pH after starting omeprazole was 5.6 (mean). The incidence of pneumonia was twelve percent. No patient in this high-risk population experienced an adverse event or a drug interaction that was attributable to omeprazole.

Conclusions

Omeprazole suspension prevented clinically significant upper gastrointestinal bleeding and maintained gastric pH above 5.5 in mechanically ventilated critical care patients without producing toxicity.

Materials and Methods

The study protocol was approved by the Institutional Review Board for the University of Missouri at Columbia.

Study Population

All adult (>18 years old) patients admitted to the surgical intensive care and burn unit at the University of Missouri Hospital with an intact stomach, a nasogastric tube in place, and an anticipated intensive care unit stay of at least forty-eight hours were considered for inclusion in the study. To be included patients also had to have a gastric pH of <4, had to be mechanically ventilated and have one of the following additional risk factors for a minimum of twenty-four hours after initiation of omeprazole suspension: head injury with altered level of consciousness, extensive burns (>20% Body Surface Area), acute renal failure, acid-base disorder, multiple trauma, coagulopathy, multiple operative procedures, coma, hypotension for longer than one hour or sepsis (see Table 2). Sepsis was defined as the presence of invasive pathogenic organisms or their toxins in blood or tissues resulting in a systematic response that included two or more of the following: temperature greater than 38° C. or less than 36° C., heat rate greater than 90 beats/minute, respiratory rate greater than 20 breaths/minute (or $_pO_2$ less than 75 mm Hg), and white blood cell count greater than 12,000 or less than 4000 cells/$mm^3$ or more than 10 percent bands (Bone, 1991). Patients in whom $H_2$-antagonist therapy had failed or who experienced an adverse event while receiving $H_2$-antagonist therapy were also included.

Patients were excluded from the study if they were receiving azole antifungal agents through the nasogastric tube; were likely to swallow blood (e.g., facial and/or sinus fractures, oral lacerations); had severe thrombocytopenia (platelet count less than 30,000 cells/$mm^3$); were receiving enteral feedings through the nasogastric tube; or had a history of vagotomy, pyloroplasty, or gastroplasty. In addition, patients with a gastric pH above four for forty-eight hours after ICU admission (without prophylaxis) were not eligible for participation. Patients who developed bleeding within the digestive tract that was not stress-related mucosal damage (e.g., endoscopically verified variceal bleeding or Mallory-Weiss tears, oral lesions, nasal tears due to placement of the nasogastric tube) were excluded from the efficacy evaluation and categorized as having non-stress-related mucosal bleeding. The reason for this exclusion is the confounding effect of non-stress-related mucosal bleeding on efficacy-related outcomes, such as the use of nasogastric aspirate inspection to define clinically significant upper gastrointestinal bleeding.

Study Drug Administration

Omeprazole solution/suspension was prepared immediately before administration by the patient's nurse using the following instructions: 1) Empty the contents of one or two 20 mg omeprazole capsule(s) into an empty 10 ml syringe (with 20 gauge needle in place) from which the plunger has been removed. (Omeprazole delayed-release capsules, Merck & Co., Inc., West Point, Pa.). 2) Replace the plunger and uncap the needle. 3) Withdraw 10 ml of 8.4% sodium bicarbonate solution or 20 ml if 40 mg given (Abbott Laboratories, North Chicago, Ill.). The resultant preparation should contain 2 mg omeprazole per ml of 8.4% sodium bicarbonate. 4) Allow the enteric coated pellets of omeprazole to completely breakdown, ~30 minutes (agitation is helpful). The omeprazole in the resultant preparation is partially dissolved and partially suspended. The preparation should have a milky white appearance with fine sediment and should be shaken before using. The solution/suspension was not administered with acidic substances. A high pressure liquid chromatography study was performed that has demonstrated that this preparation of simplified omeprazole suspension maintains >90% potency for seven days at room temperature. This preparation remained free of bacterial and fungal contamination for thirty days when stored at room temperature (see Table 5).

The initial dose of omeprazole solution/suspension was 40 mg, followed by a second 40 mg dose 6-8 hours later, then a 20 mg daily dose administered at 8:00 AM. Each dose was administered through the nasogastric tube. The nasogastric tube was then flushed with 5-10 ml of tap water and clamped for at least one hour. Omeprazole therapy was continued until there was no longer a need for stress ulcer prophylaxis (usually after the nasogastric tube removed and the patient was taking water/food by mouth, or after the patient was removed from mechanical ventilation).

Primary Outcome Measures

The primary outcome measure in this study was the rate of clinically significant stress-related mucosal bleeding defined as endoscopic evidence of stress-related mucosal bleeding or bright red blood per nasogastric tube that did not clear after a 5-minute lavage or persistent Gastroccult (SmithKline Diagnostics, Sunnyville, Calif.) positive coffee ground material for four consecutive hours that did not clear with lavage (at least 100 ml) and produced a 5% decrease in hematocrit.

Secondary Outcome Measures

The secondary efficacy measures were gastric pH measured four hours after omeprazole was administered, mean gastric pH after starting omeprazole and lowest gastric pH during omeprazole administration. Gastric pH was measured immediately after aspirating gastric contents through the nasogastric tube. pH paper (pHydrion improved pH papers, Microessential Laboratory, Brooklyn, N.Y.) was used to measure gastric aspirate pH. The pH range of the test strips was 1 to 11, in increments of one pH unit. Gastric pH was measured before the initiation of omeprazole solution/suspension therapy, immediately before each dose, and every four hours between doses.

Other secondary outcome measures were incidence of adverse events (including drug interactions) and pneumonia. Any adverse event that developed during the study was recorded. Pneumonia was defined using indicators adapted from the Centers for Disease Prevention and Control definition of nosocomial pneumonia (Garner et al., 1988). According to these criteria, a patient who has pneumonia is one who has rales or dullness to percussion on physical examination of the chest or has a chest radiograph that shows new or progressive infiltrate(s), consolidation, cavitation, or pleural effusion and has at least two of the following present: new purulent sputum or changes in character of the sputum, an organism isolated from blood culture, fever or leukocytosis, or evidence of infection from a protective specimen brush or bronchoalveolar lavage. Patients who met the criteria for pneumonia and were receiving antimicrobial agents for the treatment of pneumonia were included in the pneumonia incidence figure. These criteria were also used as an initial screen before the first dose of study drug was administered to determine if pneumonia was present prior to the start of omeprazole suspension.

Cost of Care Analysis A pharmacoeconomic evaluation of stress ulcer prophylaxis using omeprazole solution/suspension was performed. The evaluation included total drug cost (acquisition and administration), actual costs associated with adverse events (e.g., psychiatry consultation for mental confusion), costs associated with clinically significant upper gastrointestinal bleeding. Total drug cost was calculated by adding the average institutional costs of omeprazole 20 mg capsules, 50 ml sodium bicarbonate vials, and 10 ml syringes with needle; nursing time (drug administration, pH monitoring); pharmacy time (drug preparation); and disposal costs. Costs associated with clinically significant upper gastrointestinal bleeding included endoscopy charges and accompanying consultation fees, procedures required to stop the bleeding (e.g., surgery, hemostatic agents, endoscopic procedures), increased hospital length of stay (as assessed by the attending physician), and cost of drugs used to treat the gastrointestinal bleeding.

Statistical Analysis

The paired t-test (two-tailed) was used to compare gastric pH before and after omeprazole solution/suspension administration and to compare gastric pH before omeprazole solution/suspension administration with the mean and lowest gastric pH value measured after beginning omeprazole.

Results

Figure 2:
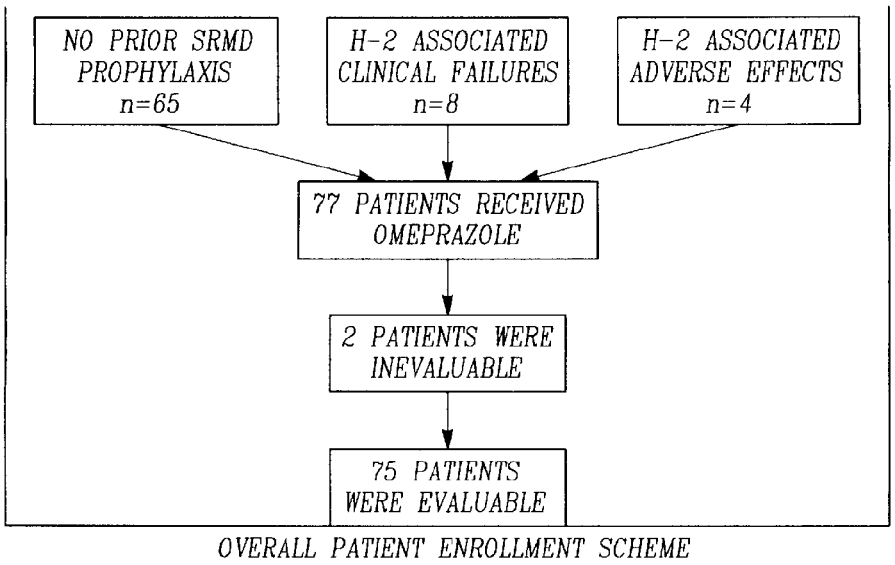
FIG. 2 is a flow chart illustrating a patient enrollment scheme.

Seventy-seven patients met the inclusion and exclusion criteria and received omeprazole solution/suspension (see FIG. 2). Two patients were excluded from the efficacy evaluation because the protocol for omeprazole administration was not followed. In one case, the omeprazole enteric-coated pellets had not completely broken down prior to the administration of the first two doses, which produced an erratic effect on gastric pH. The gastric pH increased to above six as soon as the patient was given a dose of omeprazole solution/suspension (in which the enteric coated pellets of omeprazole had been allowed to completely breakdown).

The reason for the second exclusion was that nasogastric suctioning was not turned off after the omeprazole dose was administered. This resulted in a transient effect on gastric pH. The suction was turned off with subsequent omeprazole doses, and control of gastric pH was achieved. Two patients were considered efficacy failures because omeprazole failed to maintain adequate gastric pH control on the standard omeprazole 20 mg/day maintenance dose. When the omeprazole dose 20 was increased to 40 mg/day (40 mg once/day or 20 mg twice/day), gastric pH was maintained above four in both patients. These two patients were included in the safety and efficacy evaluations, including the gastric pH analysis. After the two patients were declared failures, their pH values were no longer followed.

The ages of the remaining seventy-five patients ranged from eighteen to eighty-seven years; forty-two patients were male and thirty-three were female. All patients were mechanically ventilated during the study. Table 2 shows the frequency of risk factors for stress-related bleeding that were exhibited by the patients in this study. The most common risk factors in this population were mechanical ventilation and major surgery. The range of risk factors for any given patient was two to ten, with a mean of 3 (±1) (standard deviation). Five patients enrolled in the study had developed clinically significant bleeding while receiving continuous infusions of ranitidine (150 mg/24 hr) or cimetidine (900 mg/24 hr). In all five cases, the bleeding subsided and the gastric pH rose to above five within thirty-six hours after initiating omeprazole therapy. Three patients were enrolled after having developed two consecutive gastric pH values below three while receiving an $H_2$-antagonist (in the doses outlined above). In all three cases, gastric pH rose to above five within four hours after omeprazole therapy was initiated. Four other patients were enrolled in this study after experiencing confusion (n=2) or thrombocytopenia (n=2) during $H_2$-antigens therapy. Within thirty-six hours of switching therapy, these adverse events resolved.

Stress-related Mucosal Bleeding and Mortality

None of the sixty-five patients who received simplified omeprazole suspension as their initial prophylaxis against stress-related mucosal bleeding developed overt or clinically significant upper gastrointestinal bleeding. In four of the five patients who had developed upper gastrointestinal bleeding before study entry, bleeding diminished to the presence of occult blood only (Gastroccult-positive) within eighteen hours of starting omeprazole suspension; bleeding stopped in all patients within thirty-six hours. The overall mortality rate in this group of critically ill patients was eleven percent. No death was attributable to upper gastrointestinal bleeding or the use of omeprazole solution/suspension.

Gastric pH

Figure 3:
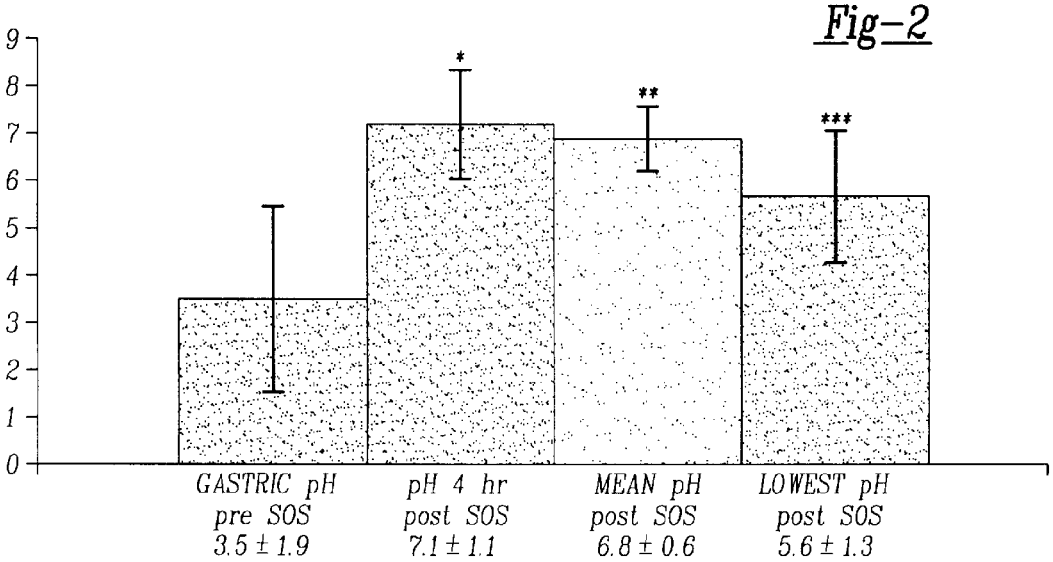
FIG. 3 is a bar graph illustrating gastric pH both pre- and post- administration of omeprazole solution/suspension according to the present invention.

The mean (±standard deviation) pre-omeprazole gastric pH was 3.5±1.9. Within four hours of omeprazole administration, the gastric pH rose to 7.1±1.1 (se FIG. 3); this difference was significant ($p<0.001$). The differences between pre-omeprazole gastric pH and the mean and lowest gastric pH measurements during omeprazole administration (6.8±0.6 and 5.6±1.3, respectively) were also statistically significant ($p<0.001$).

Safety

Omeprazole solution/suspension was well tolerated in this group of critically ill patients. Only one patient with sepsis experienced an adverse event that may have been drug-related thrombocytopenia. However, the platelet count continued to fall after omeprazole was stopped. The platelet count then returned to normal despite reinstitution of omeprazole therapy. Of note, one patient on a jet ventilator continuously expelled all liquids placed in her stomach up and out through her mouth, and thus was unable to continue on omeprazole. No clinically significant drug interactions with omeprazole were noted during the study period. As stated above, metabolic alkalosis is a potential concern in patients receiving sodium bicarbonate. However, the amount of sodium bicarbonate in omeprazole solution/suspension was small (~12 mEq/10 ml) and no electrolyte abnormalities were found.

Pneumonia

Pneumonia developed in nine (12%) patients receiving omeprazole solution/suspension. Pneumonia was present in an additional five patients before the start of omeprazole therapy.

Pharmacoeconomic evaluation

The average length of treatment was nine days. The cost of care data are listed in Tables 3 and 4. The costs of drug acquisition, preparation, and delivery for some of the traditional agents used in the prophylaxis of stress-related upper gastrointestinal bleeding are listed in Table 3. There were no costs to add from toxicity associated with omeprazole solution/suspension. Since two of seventy-five patients required 40 mg of omeprazole solution/suspension daily to adequately control gastric pH, the acquisition/preparation cost should reflect this. The additional 20 mg of omeprazole with vehicle adds seven cents per day to the cost of care. Therefore, the daily cost of care for omeprazole solution/suspension in the prophylaxis of stress-related mucosal bleeding was $12.60 see Table 4.

Omeprazole solution/suspension is a safe and effective therapy for the prevention of clinically significant stress-related mucosal bleeding in critical care patients. The contribution of many risk factors to stress-related mucosal damage has been challenged recently (6). All of the patients in this study had at least one risk factor that has clearly been associated with stress-related mucosal damage—mechanical ventilation. Previous trials and data from a recently published study show that stress ulcer prophylaxis is of proven benefit in patients at risk and, therefore, it was thought to be unethical to include a placebo group in this study. No clinically significant upper gastrointestinal bleeding occurred during omeprazole solution/suspension therapy. Gastric pH was maintained above 4 on omeprazole 20 mg/day in seventy-three of seventy-five patients. No adverse events or drug interaction associated with omeprazole were encountered.

EXAMPLE IV

The anti-microbial or bacteriostatic effects of the omeprazole solution/suspension were analyzed by applicants.

An omeprazole solution/suspension made according to the present invention was stored at room temperature for four weeks and then was analyzed for fungal and bacterial growth.

Results

Following four weeks of storage at room temperature, no bacterial or fungal growth was detected.

An omeprazole solution/suspension made in accordance with the present invention was stored at room temperature for twelve weeks and then was analyzed for fungal and bacterial growth.

Results

After twelve weeks of incubation at room temperature, no fungal or bacterial growth was detected.

The results of these experiments illustrate the stability and bacteriostatic characteristics of the omeprazole solution/suspension of the present invention.

Throughout this application various publications and patents are referenced by citation and number. Full citations for the publication are listed below. The disclosure of these publications and patents in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

TABLE I

| | ng1 | ng2 | ng3 | ng4 | ng5 | ng6 | ng7 | ng8 | ng9 |
|---|---|---|---|---|---|---|---|---|---|
| [1] gf Pre SOS | 1.3 | 1.3 | 1.3 | 1.3 | 1.3 | 1.3 | 1.3 | 1.3 | 1.3 |
| [2] gf p 1st dose 1.3←check of fg pH | 1.3 | 1.3 | 1.3 | 1.3 | 1.3 | 1.3 | 1.3 | 1.3 | 1.3 |
| [3] gf p 2nd dose 1.3←check of gf pH | 1.3 | 1.3 | 1.4 | 1.4 | 1.4 | 1.3 | 1.4 | 1.3 | 1.3 |
| | | | | | | | SOS pH = 9.0 | | |

TABLE 2

| Mech Vent | Major Surgery | Multi-trauma | Head Injury | Hypo-tension | Renal Failure | Sepsis | Multiple Operation | Acid/ Base | Coma | Liver Failure | Burn |
|---|---|---|---|---|---|---|---|---|---|---|---|
| 75 | 61 | 35 | 16 | 14 | 14 | 14 | 12 | 10 | 4 | 2 | 2 |

Risk factors present in patients in this study (n = 75)

TABLE 3

| | | Per day |
|---|---|---|
| RANITIDINE (day 1-9) | | |
| Ranitidine | 150 mg/24 hr | 6.15 |
| Ancillary Product (1) | Piggyback (60%) | 0.75 |
| Ancillary Product (2) | micro tubing (etc.) | 2.00 |
| Ancillary Product (3) | filter | .40 |
| Sterile Prep required | yes | |
| R.N. time ($24/hr) | 20 minutes/day (includes pH monitoring) | 8.00 |
| R.Ph. time, hood maint. | 3 minutes ($40/hr) | 2.00 |
| Pump cost | $29/24 hrs × 50% | 14.50 |
| TOTAL for 9 days | → | 304.20 |
| RAINITIDINE Cost per day | → | 33.80 |
| CIMETIDINE (day 1-9) | | |
| Cimetidine | 900 mg/24 hr | 3.96 |
| Ancillary Product (1) | Piggyback | 1.25 |
| Ancillary Product (2) | micro tubing (etc.) | 2.00 |
| Ancillary Product (3) | filter | .40 |
| Sterile Prep required | yes | |

TABLE 3-continued

| | | Per day |
|---|---|---|
| R.N. time ($24/hr) | 20 minutes/day (includes pH monitoring) | 8.00 |
| R.Ph. time, hood maint. | 3 minutes ($40/hr) | 2.00 |
| Pump cost | $29/24 hrs × 50% | 14.50 |
| TOTAL for 9 days | → | 288.99 |
| CIMETIDINE Cost per day | → | 32.11 |
| SUCRALFATE (day 1-9) | | |
| Sucralfate | 1 Gm × 4 | 2.40 |
| Ancillary Product (1) | syringe | .20 |
| Sterile Prep required | no | |
| R.N. time ($24/hr) | 30 minutes/day (includes pH monitoring) | 12.00 |
| TOTAL for 9 days | → | 131.40 |
| SUCRALFATE Cost per day | → | 14.60 |

Note:

Does not include the cost of failure and/or adverse effect.

Acquisition, preparation and delivery costs of traditional agents.

TABLE 4

The average length of treatment was 9 days.
Cost of care was calculated from these data:

| | | Per day | Total |
|---|---|---|---|
| OMEPRAZOLE (day 1) | | | |
| Product acquisition cost | 40 mg load × 2 (5.66/dose) | 11.32 | 11.32 |
| Ancillary product | materials for solution preparation | 0.41 | 0.41 |
| Ancillary product | syringe w/needle | 0.20 | 0.40 |
| Sterile preparation required | no | | |
| SOS preparation time (R.N.) | 6 minutes | 2.40 | 4.80 |
| R.N. time ($24/hr) | 21 minutes/day (includes pH monitoring) | 8.40 | 8.40 |

TABLE 4-continued

The average length of treatment was 9 days.
Cost of care was calculated from these data:

| | | Per day | Total |
|---|---|---|---|
| OMEPRAZOLE (days 2-9) | | | |
| Product acquisition cost | 20 mg per day | 2.83 | 22.65 |
| Ancillary product | materials for solution preparation | 0.41 | 0.82 |
| Ancillary product | syringe w/needle | 0.20 | 1.60 |
| Sterile preparation required | no | | |
| SOS preparation time (R.N.) | 6 minutes | 2.40 | 4.80 |
| R.N. time ($24/hr) | 18 minutes/day (includes pH monitoring) | 8.40 | 57.60 |

TABLE 4-continued

| The average length of treatment was 9 days. Cost of care was calculated from these data: | | |
|---|---|---|
| | Per day | Total |
| 2/75 patient require 40 mg simplified omeprazole solution per day (days 2-9) | | 0.63 |
| No additional cost for adverse effects or for failure | | |
| TOTAL → | 113.43 | |
| Simplified Omerprazole Solution Cost per day → | 12.60 | |

Pharmacoeconomic evaluation of omeprazole cost of care

TABLE 5

| Time | Control | 1 hour | 24 hour | 2 day | 7 day | 14 day |
|---|---|---|---|---|---|---|
| Conc(mg/ml) | 2.01 | 2.07 | 1.94 | 1.96 | 1.97 | 1.98 |

Stability of Simplified Omeprazole Solution at room temperature (25° C.)
Values are the mean of three samples

REFERENCES

The American Medical Association Drug Evaluation, Volume II-Gastrointestinal Drugs; In Bennett D. R. , Dickson B. D. (eds), The American Medical Association, Chicago 1:8.

Andersson et al., "Pharmacokinetics of [14C] omeprazole in patients with liver cirrhosis" Clin. Pharmacokinet, Jan.; 24 (1): 71-8 (1993).

Andersson et al., "Pharmacokinetics and bioavailability of omerprazole after single and repeated oral administration in healthy subjects" Br. J. Clin. Pharmacol., May; 29 (5): 557-63 (1990).

Andersson et al., "Pharmacokinetics of various single intravenous and oral doses of omeprazole" Eur. J. Clin. Pharmacol, 39 (2): 195-7 (1990).

Ballesteros et al., "Bolus or intravenous infusion of ranitidine: Effects on gastric pH and acid secretion: A comparison of relative cost and efficacy" Ann. Intern. Med., 112: 334-339 (1990).

Barie and Hariri, "Therapeutic use of omeprazole for refractory stress-induced gastric mucosal hemorrhage" Crit. Care Med., 20: 899-901 (1992).

Bone, "Let's agree on terminology: Definitions of sepsis" Crit. Care Med., 19: 27 (1991).

Borrero et al., "Antacids vs. sucralfate in preventing acute gastrointestinal tract bleeding in abdominal aortic surgery" Arch. Surg., 121: 810-812 (1986).

Brunton, "Agents for the control of gastric acidity and treatment of peptic ulcers. In, The pharmacologic basis of therapeutics. (eds Goodman A. G., Rall T. W., Nies A. S., Taylor P.) New York, p/907 (1990).

Cantu and Korek, "Central nervous system reactions to histamine-2 receptor blockers" Ann Intern Med., 114: 1027-1034 (1991).

Cioffi et al., "Comparison of acid neutralizing and non-acid neutralizing stress ulcer prophylaxis in thermally injured patients" J. Trauma, 36: 541-547 (1994).

Cook et a., "Risk factors for gastrointestinal bleeding in critically ill patients" N. Engl. J. Med., 330: 377-381 (1994).

Cook et al., "Stress ulcer prophylaxis in the critically ill: A meta-analysis" Am. J. Med., 91: 519-527 (1991).

Cook et al., "Nasocomial pneumonia and the role of gastric pH: A meta-analysis." Chest, 100: 7-13 (1991).

Czaja et al., "Acute gastroduodenal disease after thermal injury: An endoscopic evaluation of incidence and natural history" N Engl. J. Med. 291: 925-929 (1974).

Dobkin et al., "Does pH paper accurately reflect gastric pH?" Crit. Care Med., 18: 985-988 (1990).

Driks et al., "Nosocomial pneumonia in intubated patients given sucralfate as compared with antacids or histamine type 2 blockers" N. Engl., J. Med., 317: 1376-1382 (1987).

Eisenberg et al., "Prospective trial comparing a combination pH probe-nasogastric tube with aspirated gastric pH in intensive care unit patients" Crit. Care Med., 18: 1092-1095 (1990).

Fabian et al., "Pneumonia and stress ulceration in severely injured patients" Arch. Surg. , 128: 185-191 (1993).

Fellenius et al., "Substituted benzimidazoles inhibit gastric acid secretion by blocking H+/K+−ATPase" Nature, 290: 159-161(1981).

Fiddian-Green e al., "Predictive value of intramural pH and other risk factors for massive bleeding from stress ulceration" Gastroenterology, 8: 613-620 (1983).

Fryklund et al., "Function and structure of parietal cells after H+/K+−ATPase blockade" Am. J. Physiol., 254 (3 pt 1); G399-407 (1988).

Gafter et al., "Thrombocytopenia associated with hypersensitivity to ranitidine: possible cross-reactivity with cimetidine" Am. J. Gastroenterol, 64: 560-562 (1989).

Garner et al., "CDC definitions for nosocomial infections" Am. J. Infect. Control, 16: 128-140 (1988).

Heath et al., "Intragastric pH measurement using a novel disposable sensor" Intens. Care Med., 14: 232-235 (1988).

Kiilerich et al., "Effect of intravenous infusion of omeprazole and ranitidine on twenty-four-hour intragastric pH in patients with a history of duodenal ulcer" Digestion, 56: 25-30 (1995).

Laggner et al., "Prevention of upper gastrointestinal bleeding in long-term ventilated patients" Am. J. Med., 86 (suppl 6A): 81-84 (1989).

Landahl et al., "Pharmacokinetic study of omeprazole in elderly healthy volunteers" Clin. Pharmacokinet, Dec.; 23 (6): 469-76 (1992).

Larson et al., "Gastric response to severe head injury" Am. J. Surg. 147: 97-105 (1984).

Marrone and Silen, "pathogenesis, diagnosis and treatment of acute gastric mucosa lesions" Clin Gastroenterol 13: 635-650 (1984).

Martin et al., "Continuous intravenous cimetidine decreases stress-related upper gastrointestinal hemorrhage without promoting pneumonia. Crit Care Med., 21: 19-39 (1993).

Martin et al., "Stress ulcers and organ failure in intubated patients in surgical intensive care units" Ann Surg., 215: 332-337 (1992).

Meiners et al., "Evaluation of various techniques to monitor intragastric pH" Arch. Surg., 117: 288-291 (1982).

Oh and Carroll, "Electrolyte and acid-base disorders. In, The pharmacologic approach to the critically ill patient (ed. Chernow B.) Williams & Wilkins, Baltimore, pp. 966-967 (1994).

Ostro et al., "Control of gastric pH with cimetidine boluses versus primed infusions" Gastroenterology, 89: 532-537 (1985).

Peura and Johnson, "Cimetidine for prevention and treatment of gastroduodenal mucosal lesions in patients in an intensive care unit. Ann Intern Med., 103: 173-177 (1985).

Phillips and Metzler, "Simplified omeprazole solution for the prophylaxis of stress-related mucosal damage in critically ill patients" Crit. Care Med., 22: A53 (1994).

Pickworth et al., "Occurrence of nasocomial pneumonia in mechanically ventilated trauma patients: A comparison of sucralfate and ranitidine" Crit. Care Med., 12: 1856-1862 (1993).

Pilbrant et al., "Development of an oral formulation of omeprazole" Gastroenterol Suppl., 108: 113-20 (1985).

Priebe and Skillman, "Methods of prophylaxis in stress ulcer disease" World J. Surg., 5: 223-233 (1981).

Regardh et al., "The pharmacokinetics of omeprazole in humans—a study of single intravenous and oral doses" Ther. Drug Monit, Mar.; 12 (2): 163-72 (1990).

Ryan et al., "Nasocomial pneumonia during stress ulcer prophylaxis with cimetidine and sucralfate" Arch. Surg., 128: 1353-1357 (1993).

Sax, "Clinically important adverse effects and drug interactions with H2-receptor antagonists: An update" Pharmacotherapy 7(6 pt 2): 110S-115S (1987).

Schepp, "Stress ulcer prophylaxis: Still a valid option in the 1990s?" Digestion 54: 189-199 (1993).

Schuman et al., "Prophylactic therapy for acute ulcer bleeding: A reappraisal." Ann Intern. Med, 106: 562-567 (1987).

Schuster, "Stress ulcer prophylaxis: in whom? with what?" Crit. Care Med. 21: 4-6 (1993).

Siepler, "A dosage alternative for H-2 receptor antagonists, continuous-infusion" Clin. Ther., 8(Suppl A): 24-33 (1986).

Simms et al., "Role of gastric colonization in the development of pneumonia in critically ill trauma patients: Results of a prospective randomized trial" J. Trauma, 31: 531-536 (1991).

Skillman et al., "Respiratory failure, hypotension, sepsis and jaundice: A clinical syndrome associated with lethal hemorrhage from acute stress ulceration" Am. J. Surg., 117: 523-530 (1969).

Skillman et al., "The gastric mucosal barrier: Clinical and experimental studies in critically ill and normal man and in the rabbit" Ann Surg., 172: 564-584 (1970).

Smythe and Zarowitz, "Changing perspectives of stress gastritis prophylaxis" Ann Pharmacother, 28: 1073-1084 (1994).

Spychal and Wickham, "Thrombocytopenia associated with ranitidine" Br. Med. J., 291: 1687 (1985).

Tryba, "Stress ulcer prophylaxis—quo vadis? Intens. Care Med. 20: 311-313 (1994).

Tryba, " Risk of acute stress bleeding and nosocomial pneumonia in ventilated intensive care patients. Sucralfate vs. antacids" Am. j. Med., 87(3B): 117-124(1987).

Vial et al., "Side effects of ranitidine" Drug Saf, 6: 94-117 (1991).

Wallmark et al, "The relationship between gastric acid secretion and gastric H+/K+–ATPase activity" J. Biol.Chem., 260: 13681-13684 (1985).

Wilder-Smith and Merki, "Tolerance during dosing with $H_2$-receptor antagonists. An overview. Scand. J. Gastroenterol 27(suppl 193): 14-19 (1992).

Zinner et al., "The prevention of gastrointestinal tract bleeding in patients in an intensive care unit" Surg. Gynecol. Obstet., 153: 214-220 (1981).

We claim:

1. A method for treating gastric acid disorders *selected from the group consisting of active duodenal ulcers, gastric ulcers, gastroesophageal reflux disease* (*GERD*), *severe erosive esophagitis, poorly responsive systematic GERD, and Zollinger Ellison Syndrome* by administering to a patient *in* a single dose [of] a pharmaceutical composition of omeprazole or lansoprazole *powder* in a pharmaceutically acceptable carrier consisting essentially of a bicarbonate salt of a Group IA metal wherein said administering step consists of providing to the patient orally *in* a single dose of [of] an aqueous solution or[,] suspension of the pharmaceutical composition without requiring further administration of the bicarbonate salt of the Group IA metal, *wherein upon oral administration of the suspension at least some of the omeprazole or lansoprazole is absorbed within about 10 to about 12 minutes after administration.*

2. A method according to claim 1, wherein the Group IA metal is sodium.

3. A method according to claim 1, wherein the Group IA metal is potassium.

4. A method according to claim 1, wherein the concentration of omeprazole in the composition [range] *ranges* from approximately 0.5 mg/ml to approximately 6.0 mg/ml.

5. A method according to claim 3, wherein the concentration of omeprazole in said composition [range] *ranges* from approximately 1.0 mg/ml to approximately 4.0 mg/ml.

6. A method as set forth in claim 5, wherein the concentration of omeprazole in the composition is approximately 2.0 mg/ml.

7. A method as set forth in claim 1, wherein the concentration of the bicarbonate salt of the Group IA metal in the composition ranges from approximately 5.0% to approximately 60.0%.

8. A method as set forth in claim 7, wherein the concentration of the bicarbonate salt of the Group IA metal in the composition ranges from approximately 7.5% to approximately 10.0%.

9. A method as set forth in claim 8, wherein the concentration of the bicarbonate salt of the Group IA metal is approximately 8.4%.

10. A method as set forth in claim 1, wherein the [single dosage form] *pharmaceutical composition* includes a concentration of bicarbonate ranging from approximately 0.75 [meq] *mEq* to 1.5 [meq] *mEq* per milliliter.

11. A method as set forth in claim 10, wherein the amount of the bicarbonate in the [single dosage form] *pharmaceutical composition* is less than approximately 12 [mEq/20] *mEq per 20* mg [dose] of omeprazole.

12. A method as set forth in claim 1, wherein the [single dosage form] *pharmaceutical composition* is administered in a volume of between approximately 10 ml and 20 ml.

*13. A method for treating gastric acid disorders selected from the group consisting of active duodenal ulcers, gastric ulcers, gastroesophageal reflux disease* (*GERD*), *severe erosive esophagitis, poorly responsive systematic GERD, and Zollinger Ellison Syndrome by administering to a patient in a single dose a pharmaceutical composition of omeprazole powder in a pharmaceutically acceptable carrier consisting essentially of a bicarbonate salt of a Group IA metal wherein said administering step consists of providing to the patient orally in a single dose an aqueous solution or suspension of the pharmaceutical composition without requiring further administration of the bicarbonate salt of the Group IA metal, wherein the concentration of omeprazole in said composition ranges from approximately 1.0 mg/ml to approximately 4.0 mg/ml.*

*14. A method for treating gastric acid disorders selected from the group consisting of active duodenal ulcers, gastric ulcers, gastroesophageal reflux disease* (*GERD*), *severe erosive esophagitis, poorly responsive systematic GERD, and Zollinger Ellison Syndrome by administering to a patient in a single dose a pharmaceutical composition of omeprazole powder in a pharmaceutically acceptable carrier consisting essentially of a bicarbonate salt of a Group IA metal wherein said administering step consists of providing to the patient orally in a single dose an aqueous solution or suspension of the pharmaceutical composition without requiring further*

*administration of the bicarbonate salt of the Group IA metal, wherein the concentration of omeprazole in said composition is approximately 2.0 mg/ml.*

*15. A method for treating gastric acid disorders selected from the group consisting of active duodenal ulcers, gastric ulcers, gastroesophageal reflux disease (GERD), severe erosive esophagitis, poorly responsive systematic GERD, and Zollinger Ellison Syndrome by administering to a patient in a single dose a pharmaceutical composition of omeprazole powder in a pharmaceutically acceptable carrier consisting essentially of a bicarbonate salt of a Group IA metal wherein said administering step consists of providing to the patient orally in a single dose an aqueous solution or suspension of the pharmaceutical composition without requiring further administration of the bicarbonate salt of the Group IA metal, wherein the amount of the bicarbonate in the single dose is less than approximately 12 mEq/20 mg dose of omeprazole.*

*16. A method for treating gastric acid disorders selected from the group consisting of active duodenal ulcers, gastric ulcers, gastroesophageal reflux disease (GERD), severe erosive esophagitis, poorly responsive systematic GERD, and Zollinger Ellison Syndrome by administering to a patient in a single dose a pharmaceutical composition of omeprazole or lansoprazole powder in a pharmaceutically acceptable carrier consisting essentially of a bicarbonate salt of a Group IA metal wherein said administering step consists of providing to the patient orally in a single dose an aqueous solution or suspension of the pharmaceutical composition without requiring further administration of the bicarbonate salt of the Group IA metal, wherein the single dose is administered in a volume of between approximately 10 ml and approximately 20 ml.*

*17. The method of claim 1, wherein the solution or suspension further includes a thickening agent.*

*18. The method of claim 17, wherein the pharmaceutically acceptable carrier consists essentially of sodium bicarbonate.*

*19. The method of claim 17, wherein the sodium bicarbonate is present in an amount of approximately 0.75 mEq (mmol) to approximately 1.5 mEq (mmol) sodium bicarbonate per 2 mg of omeprazole powder.*

*20. The method of claim 18, wherein the sodium bicarbonate is present in an amount of approximately 0.75 mEq (mmol) to approximately 1.5 mEq (mmol) sodium bicarbonate per 2 mg of omeprazole powder.*

*21. The method of claim 19, wherein the omeprazole powder is present in an amount of about 20 mg per 10 ml solution.*

*22. The method of claim 20, wherein the omeprazole powder is present in an amount of about 20 mg per 10 ml solution.*

*23. The method of claim 21, wherein upon oral administration a therapeutically effective amount of the omeprazole is absorbed within about 10 to about 12 minutes after administration.*

*24. The method of claim 22, wherein upon oral administration a therapeutically effective amount of the omeprazole is absorbed within about 10 to about 12 minutes after administration.*

* * * * *